US010981961B2

(12) United States Patent
Ildefonso et al.

(10) Patent No.: US 10,981,961 B2
(45) Date of Patent: Apr. 20, 2021

(54) DELIVERY OF CARD PROTEIN AS THERAPY FOR OCCULAR INFLAMMATION

(71) Applicant: University of Florida Research Foundation, Incorporated, Gainesville, FL (US)

(72) Inventors: Cristhian J. Ildefonso, Gainesville, FL (US); Alfred S. Lewin, Gainesville, FL (US); Qiuhong Li, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 14/775,289

(22) PCT Filed: Mar. 11, 2014

(86) PCT No.: PCT/US2014/023262
§ 371 (c)(1),
(2) Date: Sep. 11, 2015

(87) PCT Pub. No.: WO2014/164703
PCT Pub. Date: Oct. 9, 2014

(65) Prior Publication Data
US 2016/0017012 A1    Jan. 21, 2016

(51) Int. Cl.
*C07K 14/47* (2006.01)
*A61K 48/00* (2006.01)
(Continued)

(52) U.S. Cl.
CPC ........ *C07K 14/4703* (2013.01); *A61K 9/0048* (2013.01); *A61K 48/005* (2013.01);
(Continued)

(58) Field of Classification Search
CPC ...... A61K 38/00; A61K 48/00; A61K 48/005; A61K 9/0048; C07K 14/4703;
(Continued)

(56) References Cited

U.S. PATENT DOCUMENTS 6,355,618 B1 * 3/2002 Cai .................. C07C 237/22
514/16.4
6,482,933 B1 * 11/2002 Bertin ............... C07K 14/4702
435/252.1

(Continued)

FOREIGN PATENT DOCUMENTS

EP    2 000 536 A2    12/2008
WO    WO 01/00826 A1 *  1/2001
(Continued)

OTHER PUBLICATIONS

Pycard, Human Protein Atlas, 4 pages, also available at http://www.proteinatlas.org/ENSG00000103490-PYCARD/cell/CAB006853 (last visited Aug. 5, 2016).*

(Continued)

*Primary Examiner* — Randall L Beane
(74) *Attorney, Agent, or Firm* — Wolf, Greenfield & Sacks, P.C.

(57) ABSTRACT

The present invention provides methods and compositions for treating and/or preventing age related macular degeneration and other conditions involving macular degeneration, ocular neovascularization, or ocular inflammation. In an exemplary embodiment, a method is disclosed that involves administering an expression vector that delivers a secretable and cell penetrating CARD to a subject in need of treatment or prevention of age-related macular degeneration or another condition involving macular degeneration or ocular neovascularization.

8 Claims, 14 Drawing Sheets
Specification includes a Sequence Listing.

(51) Int. Cl.
    A61K 9/00      (2006.01)
    C12N 15/86     (2006.01)
    A61K 38/00     (2006.01)
(52) U.S. Cl.
    CPC .............. A61K 38/00 (2013.01); A61K 48/00
        (2013.01); C07K 2319/02 (2013.01); C07K
        2319/03 (2013.01); C07K 2319/10 (2013.01);
        C12N 15/86 (2013.01); C12N 2740/15041
        (2013.01); C12N 2750/14141 (2013.01)
(58) Field of Classification Search
    CPC ............ C07K 2319/02; C07K 2319/03; C07K
        2319/10; C12N 15/86; C12N 2740/15041;
        C12N 2750/14141
    See application file for complete search history.

(56)                 References Cited

U.S. PATENT DOCUMENTS 6,756,196  B2 *  6/2004   Bertin ................ C07K 14/4702
                                                          435/4
    6,869,775  B2 *  3/2005   Bertin .................. C12Q 1/6897
                                                      435/252.3
    6,953,657  B2 * 10/2005   Bertin ................ C07K 14/4702
                                                          435/4
 2003/0165488  A1 *  9/2003   Kletzien .............. C12N 9/6475
                                                       424/94.63
 2005/0129685  A1    6/2005   Cao et al.
 2011/0130345  A1 *  6/2011   Rohrer ............... A61K 38/1709
                                                        514/20.8

FOREIGN PATENT DOCUMENTS

WO    WO-2010005533 A2 *  1/2010  .......... A61K 38/446
    WO    WO-2010138555 A2 * 12/2010  ............... C07K 7/14
    WO    WO 2011/032981 A1   3/2011

OTHER PUBLICATIONS

Olry et al., Renfield's Syndrome, Journal of the History of the Neurosciences, vol. 20:368-371 (2011).*
Stein, Afterbirth: It's What's for Dinner, Time. Jul. 13, 2009, vol. 174(1):60, attached as 2 pages.*
Human ASC (2KN6_A, NCBI.nlm.nih.gov, submitted Nov. 16, 2011, 2 pages, also available at http://www.ncbi.nlm.nih.gov/protein/2KN6_A (last visited Aug. 6, 2016.*
Dasuri et al., Free Radical Biology and Medicine, vol. 62:170-185 (online Sep. 19, 2012).*
Baraibar et al., Experimental Gerontology, vol. 48:620-625 (online Nov. 2, 2012).*
Palacios-Rodriguez et al., Polypeptide Modulators of Caspase Recruitment Domain (CARD)—CARD mediated Protein-Protein Interactions, The Journal of Biological Chemistry, vol. 286(52):44457-44466 (Dec. 30, 2011).*
Lubell-Snyder et al., Placentophagia: Stir-fry, Smoothie or Raw?, Midwifery Today, Winter 2011, 21-23 (2011).*
CARD16, "CARD16", ProteinAtlas.org, attached as pdf, 3 pages, also available at http://www.proteinatlas.org/ENSG00000204397-CARD16/tissue#gene_information (last visited Dec. 15, 2016).*
Martinon et al., Inflammatory Caspases:Linking an Intracellular Innate immune System to Autoinflammatory Diseases, Cell, vol. 117:561-574 (2004).*
Salminen et al., Endoplasmic Reticulum Stress in Age-Related Macular Degeneration: Trigger for Neovascularization, Mol Med, vol. 16:535-542 (2010).*
Rathinam et al., Regulation of inflammasome signaling, Nature Immunology, vol. 13(4):333-342 (Apr. 2012).*
Samardzija et al., Caspase-1 Ablation Protects Photoreceptors in a Model of Autosomal Dominant Retinitis Pigmentosa, Investigative Ophthalmology & Visual Science, vol. 47(12):5181-5190 (Dec. 2006).*
Neuss et al., The Apoptotic Regulatory Protein ARC (Apoptosis Repressor with Caspase Recruitment Domain) Prevents Oxidant Stress-mediated Cell Death by Preserving Mitochondrial Function, The Journal of Biological Chemistry, vol. 276(36):33915-33922 (Sep. 7, 2001).*
Stehlik et al., COPs and POPs: Modulators of Inflammasome Activity, Journal of Immunology, vol. 179:7993-7998 (2007)).*
Lee et al., COP, a Caspase Recruitment Domain-containing Protein and Inhibitor of Caspase-1 Activation Processing, The Journal of Biological Chemistry, vol. 276(37):34495-34500 (2001)).*
Bian et al., Regulated Expression of Caspase-12 Gene in Human Retinal Pigment Epithelial Cells Suggests Its Immunomodulating Role, Investigative Ophthalmology & Visual Science, vol. 49(12):5593-5601 (Dec. 2008)).*
An et al., TAT—Apoptosis Repressor With Caspase Recruitment Domain Protein Transduction Rescues Mice From Fulminant Liver Failure, Hepatology, vol. 56(2):715-726 (Jul. 3, 2012)).*
Zapata, The Role of Oxidative Stress in Ocular Disease, 113-131 (Feb. 4, 2011) in Studies on Veterinary Medicine. Oxidative Stress in Applied Basic Research and Clinical Practice. Humana Press, Totowa, NJ.*
Oduntan et al., A review of the role of oxidative stress in the pathogenesis of eye diseases, S. Afr. Optom., vol. 70(4):191-199 (2011).*
Johnson et al., Cell penetrating peptide POD mediates delivery of recombinant proteins to retina, cornea and skin, Vision Research, vol. 50:686-687 (2010).*
Restinitis Pigmentosa?, www.mesvision.com, 2 pages, attached as pdf, also available at https://www.mesvision.com/knowledgeCenter/retinitusPigmentosa.htm (last visited Jul. 13, 2017).*
Diabetic Retinopathy, www.mayoclinic.org, attached as pdf, 3 pages, also available at http://www.mayoclinic.org/diseases-conditions/diabetic-retinopathy/basics/prevention/con-20023311 (last visited Jul. 13, 2017).*
Srinivasula et al., The PYRIN-CARD Protein ASC Is an Activating Adaptor for Caspase-1, The Journal of Biological Chemistry, vol. 277(24):21119-21122 (2002) (Year: 2002).*
AB023416, NCBI, Genbank AB023416.2, www.ncbi.nlm.nih.gov, (Sep. 19, 2008), 2 pages, also available at https://www.ncbi.nlm.nih.gov/nuccore/AB023416 (last visited Apr. 1, 2019) (Year: 2008).*
Brooks et al., Tat peptide-mediated cellular delivery: back to the basics, Advanced Drug Delivery Reviews, vol. 57:559-577 (2005) (Year: 2005).*
Foti et al., Gene Therapy, vol. 16:1314-1319 (2009) (Year: 2009).*
Bruewer et al. (Evaluation of Lateral Spread of Transgene Expression following Subretinal AAV-Mediated Gene Delivery in Dogs, PLoS ONE 8(4): e60218. https://doi.org/10.1371/journal.pone.0060218 (published Apr. 3, 2013) (Year: 2013).*
EP 14779372.3, Sep. 21, 2016, Extended European Search Report.
PCT/US2014/023262, Aug. 26, 2014, International Search Report and Written Opinion.
PCT/US2014/023262, Sep. 24, 2015, International Preliminary Report on Patentability.
Extended European Search Report dated Sep. 21, 2016 for Application No. 14779372.3.
International Search Report and Written Opinion dated Aug. 26, 2014 in connection with International Application No. PCT/US2014/023262.
International Preliminary Report on Patentability dated Sep. 24, 2015 in connection with International Application No. PCT/US2014/023262.
Barka et al., Production of cell lines secreting TAT fusion proteins. J Histochem Cytochem. Apr. 2004;52(4):469-77.
Gustafsson et al., TAT protein transduction into isolated perfused hearts: TAT-apoptosis repressor with caspase recruitment domain is cardioprotective. Circulation. Aug. 6, 2002;106(6):735-9.
Ildefonso et al., Gene therapy with the caspase activation and recruitment domain reduces the ocular inflammatory response. Mol Ther. May 2015;23(5):875-84. doi: 10.1038/mt.2015.30. Epub Feb. 20, 2015.
Ildefonso et al., Targeting the Inflammasome with the Caspase Activation Recruitment Domain (CARD) in an In vitro Model of

(56) References Cited

OTHER PUBLICATIONS

RPE Inflammation. ARVO 2013 Annual Meeting. May 5-9, 2013. Abstract 148. Investigative Opthalmology & Visual Science Jun. 2013, vol. 54, 148.

Rosenzweig et al., The NLRP3 inflammasome is active but not essential in endotoxin-induced uveitis. Inflamm Res. Mar. 2012; 61(3): 225-231. Published online Nov. 26, 2011. doi: 10.1007/s00011-011-0404-8.

Stehlik et al., Apoptosis-associated speck-like protein containing a caspase recruitment domain is a regulator of procaspase-1 activation. J Immunol. Dec. 1, 2003;171(11):6154-63.

Tarallo et al., DICER1 loss and Alu RNA induce age-related macular degeneration via the NLRP3 inflammasome and MyD88. Cell. May 11, 2012;149(4):847-59. doi: 10.1016/j.cell.2012.03.036. Epub Apr. 26, 2012.

Tseng et al., NLRP3 inflammasome activation in retinal pigment epithelial cells by lysosomal destabilization: implications for age-related macular degeneration. Invest Ophthalmol Vis Sci. Jan. 7, 2013;54(1):110-20. doi: 10.1167/iovs.12-10655.

\* cited by examiner

```
Translation 100 a.a.  MW=11811.91000000002

1 Arg Lys Lys Arg Arg Gln Arg Arg Gln Ser Ala Ala Lys Pro Gly Leu His Phe Ile    20
1974 AGA AAG AAG CGG AGA CAG CGA CGA CAG TCG GCA GCC AAG CCA GGC CTC CAC TTT ATA  2033

21 Asp Gln His Arg Ala Ala Leu Ile Ala Arg Val Thr Asn Val Glu Trp Leu Asp Ala    40
2034 GAC CAG CAC CGG GCT GCG CTT ATC GCC AGG GTC ACA AAC GTT GAG TGG CTG GAT GCT  2093

41 Leu Tyr Gly Lys Val Leu Thr Asp Glu Gln Tyr Gln Ala Val Arg Ala Glu Pro Thr Asn  60
2094 CTG TAC GGG AAG GTC CTG ACG GAT GAG CAG TAC CAG GCA GTG CGG GCC GAG CCC ACC AAC  2153

61 Pro Ser Lys Met Arg Lys Leu Phe Ser Phe Thr Pro Ala Trp Asn Trp Thr Cys Lys Asp  80
2154 CCA AGT AAG ATG AGG AAG CTC TTC AGT TTC ACA CCA GCC TGG AAC TGG ACC TGC AAG GAC  2213

81 Leu Leu Leu Gln Ala Leu Arg Glu Ser Gln Ser Tyr Leu Val Glu Asp Leu Val Glu Arg Ser 100
2214 TTG CTC CTC CAG GCC CTA AGG GAG AGC CAG TCC TAC CTG GTG GAG GAC CTG GTG GAG CGG AGC 2273

101 End   101
2274 tga   2276
```

Figure 2

DELIVERY OF CARD PROTEIN AS THERAPY FOR OCCULAR INFLAMMATION

STATEMENT OF GOVERNMENT FUNDING

The invention was made with government support under EY020825 and EY021721 awarded by the National Institutes of Health. The government has certain rights in the invention.

CROSS-REFERENCE TO RELATED APPLICATIONS

This application is a national stage filing under 35 U.S.C. § 371 of International PCT application PCT/US2014/023262, filed Mar. 11, 2014 which is related to U.S. Provisional Application No. 61/776,076 filed Mar. 11, 2013, to which priority is claimed under 35 USC 119, and whose entire disclosures are incorporated herein by reference.

BACKGROUND AND SUMMARY

Dry Age-related macular degeneration (AMD) has been associated with an increase in oxidative stress and inflammatory processes within the retina. Oxidized molecules like 4-hydroxynonenal (4-HNE) have been detected in the eyes of dry AMD patients, supporting the role of these processes in the diseases. The purpose of this work is to develop an AAV vector that delivers a secretable and cell penetrating caspase activation and recruitment domain (CARD) from the Apoptosis-associated speck-like protein containing a CARD (ASC) gene to study the role of the proinflammatory cytokine IL-1 beta (IL-1β) in dry AMD and for developing treatments of diseases, conditions or disorders associated with oxidative stress and inflammation.

BRIEF DESCRIPTION OF THE DRAWINGS

FIG. 2. DNA sequence (SEQ ID NO: 2) and protein translation (SEQ ID NO: 1) of the fusion protein TatCARD. The sequence highlighted in dark gray corresponds to the sequence of the Tat peptide, while the sequence highlighted in light gray corresponds to the CARD domain. The predicted molecular weight (MW) of the TatCARD fused protein is 11.8 KDa based on its amino acid sequence.

Expression of TatCARD in stable cell lines. The human monocytic cell line THP-1 was selected for its known ability to secrete IL-1β upon IFN-γ and LPS induction. Cells were transduced with either LV/EF1-MCS-T2A-PuroR or LV/EF1-TatCARD-T2A-PuroR and selected with 1 microg/mL of puromycin for at least 2 week. A sample of each stable cell line and a sample of non-transduced cells (control) were lysed for protein extraction. Protein lysate was run in a 12% SDS-PAGE assay and the expression of the transgene was detected using western blot with an anti-T2A antibody. This antibody detects the attached fragment of the 2A peptide that remains fused to the transgene after self-cleavage of the T2A peptide. The TatCARD was detected in the protein lysate of TatCARD-THP1 cells only. Actin detection was used as a loading control.

Figure 1:
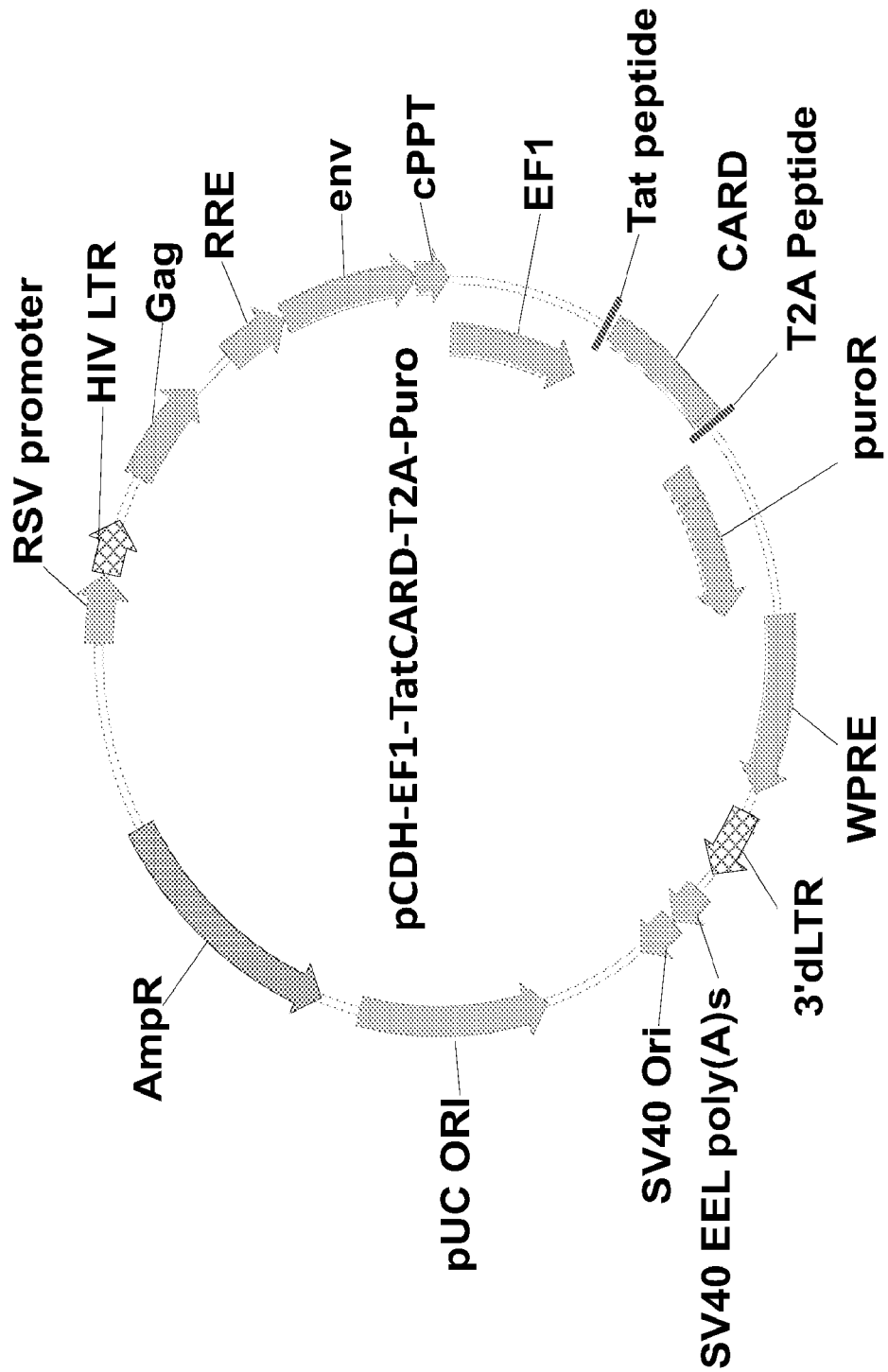
FIG. 1. Development of a lentiviral vector delivering the fused TatCARD protein. The caspase activation and recruitment domain (CARD) from the Apoptosis-associated speck-like protein containing a CARD (ASC) gene, which is known to link the NRLP3 protein of the inflammasome to the caspase-1 enzyme, was fused to the cell-penetrating peptide derived from the HIV Tat protein (Tat) by PCR. This DNA fragment was cloned into the pCDH-EF1-MCS-T2A-Puro lentiviral vector (LV) plasmid within the multiple cloning site (MCS) to create the fused gene TatCARD-T2A-PuroR. Cells transduced with the LV/EF1-TatCARD-T2A-PuroR will express the fused TatCARD-T2A-PuroR protein which will be separated into the TatCARD and PuroR proteins by the self-cleaving peptide T2A. Cells expressing the TatCARD fused protein can then be selected by their resistant to puromycin in vitro.
Figure 3:
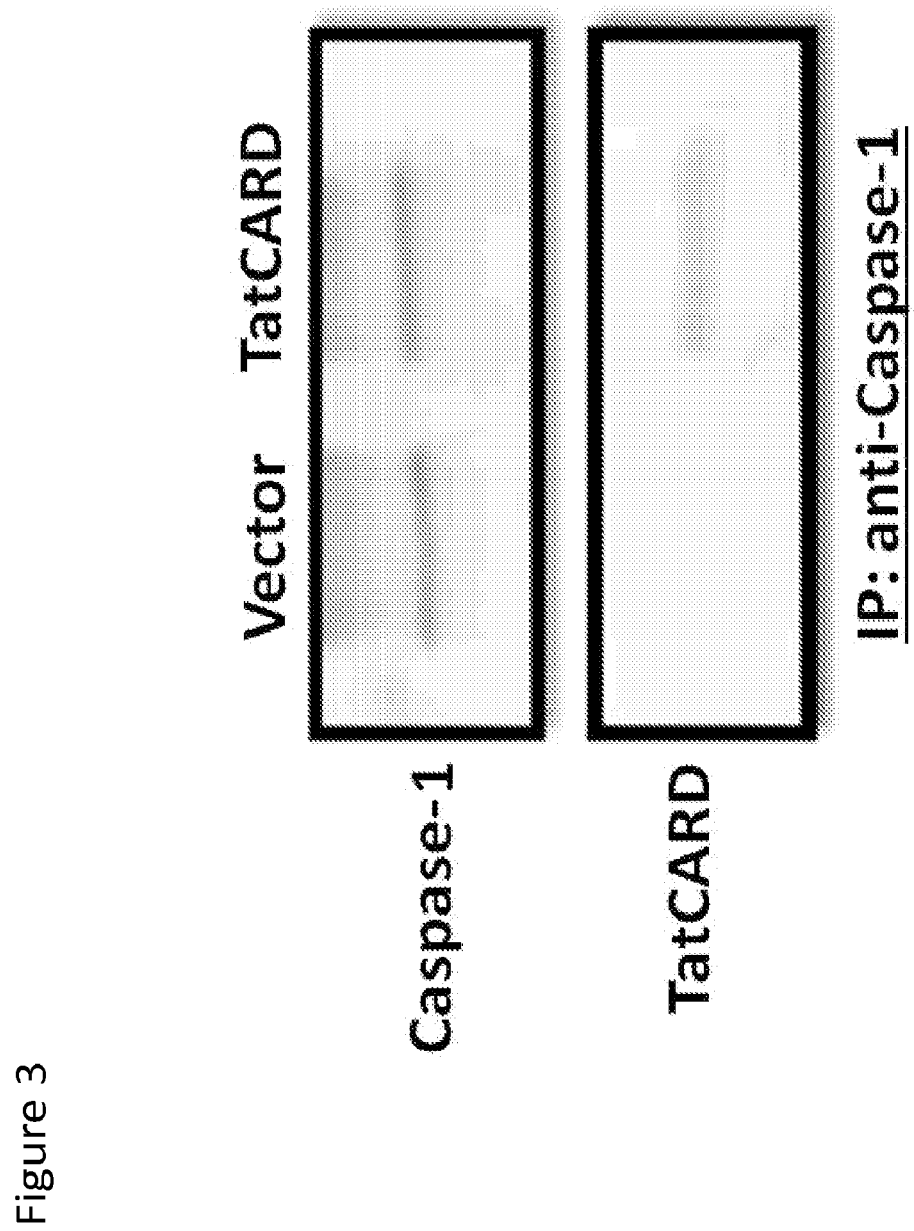
FIG. 3. The CARD domain of the ASC gene binds to caspase-1. Protein lysate from ARPE-19 transduced with lentiviral vector delivering either the puromycin resistance gene (PuroR) or the TatCARD-PuroR were subjected to caspase-1 immunoprecipitation. Immunoprecipitated samples were then separated in a 12% SDS-PAGE and transferred into a PVDF membrane. Membranes were probed with either anti-caspase-1 antibody or anti-T2A antibody (to detect TatCARD).
Figure 4:
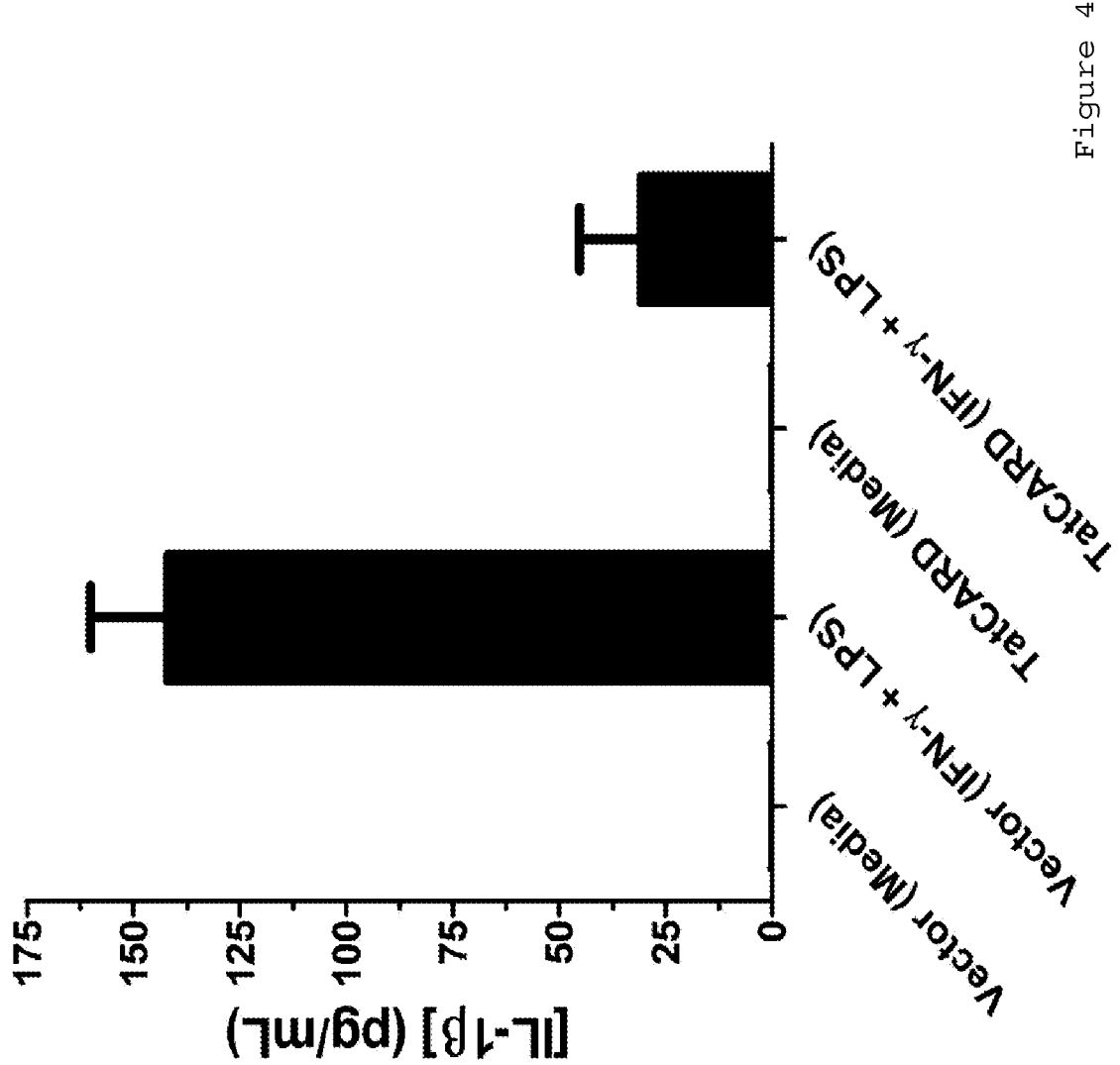

FIG. 4. Expression of the fused protein TatCARD inhibits the LPS-induced secretion of IL-1β in THP-1 cells. THP-1 cells stably expressing either the PuroR alone or the TatCARD fused protein were grown in the presence or absence of IFN-γ for 4 hours followed by incubation with or without LPS for 18 hours. Conditioned media was harvested afterwards and the levels of IL-1β were quantified by enzyme linked immunosorbent assay (ELISA). The levels of IL-1β in the absence of any stimulation (Media) were almost undetectectable by the assay. Cells expressing the TatCARD fusion protein showed a significant inhibition of IL-1β secretion when compared to cell expressing only the PuroR gene (Vector).

Figure 5:
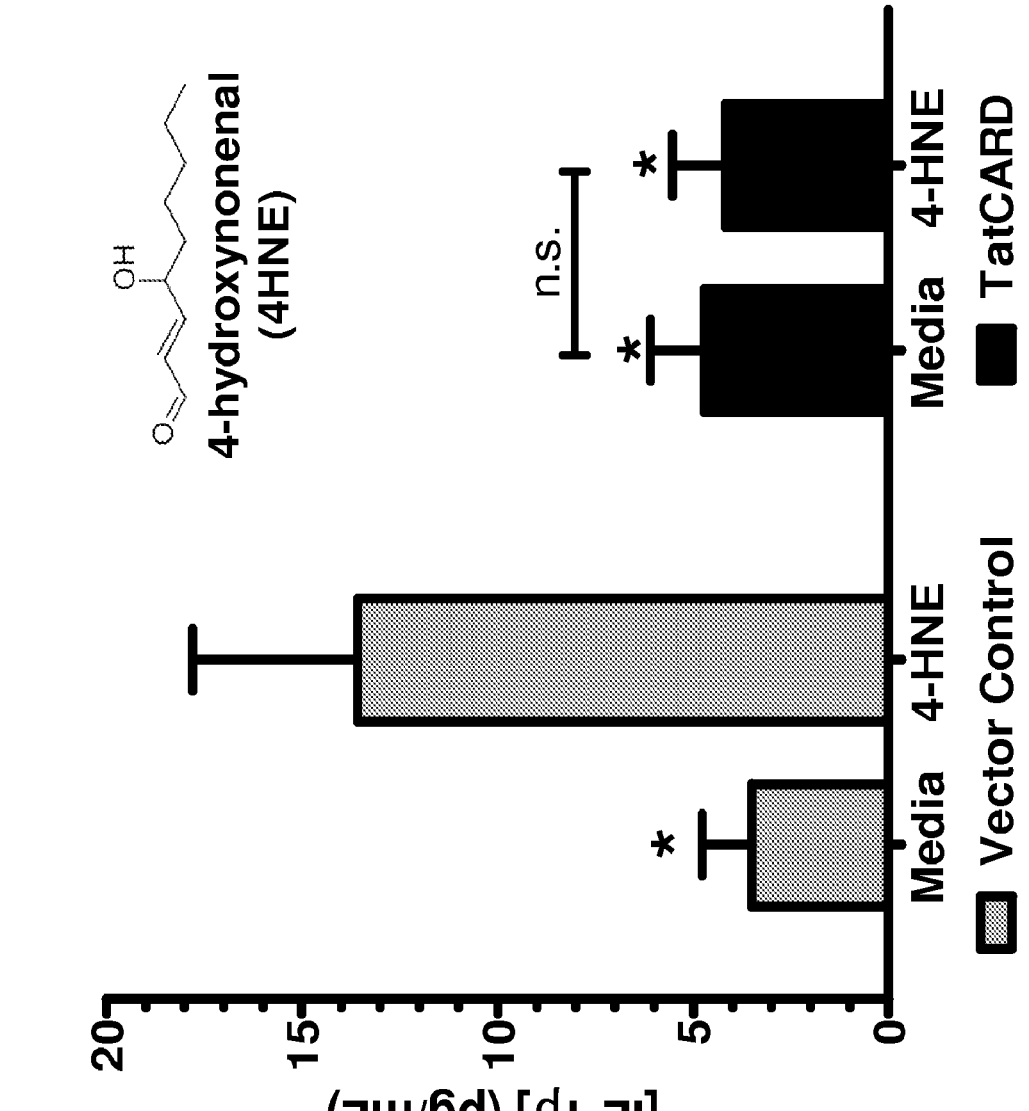

FIG. 5. Expression of TatCARD inhibits the secretion of IL-1b in an in vitro model of RPE inflammation. ARPE-19 cells expressing either the PuroR or TatCARD were stimulated with 4HNE (30 µM). The concentration of IL-1β in their conditioned media was quantified by ELISA.

Expression of the fused protein TatCARD inhibits the 4-HNE-induced secretion of IL-1β in ARPE-19 cells. The human retinal pigmented epithelium (RPE) like cells ARPE-19 were transduced with either LV/EF1-MCS-T2A-PuroR or LV/EF1-TatCARD-T2A-PuroR and selected for their resistance against puromycin. Resistant cells were grown in the presence or absence (Media) of 4-hydroxynonenal (an active aldehyde produced in dry-AMD) for 24 hours. Afterwards the levels of IL-1β in the conditioned media were determined by ELISA as done in previous experiments. The expression of the TatCARD fused protein decreased the levels of 4-HNE induced secretion of IL-1β when compared to vector control cells.

Figure 6:
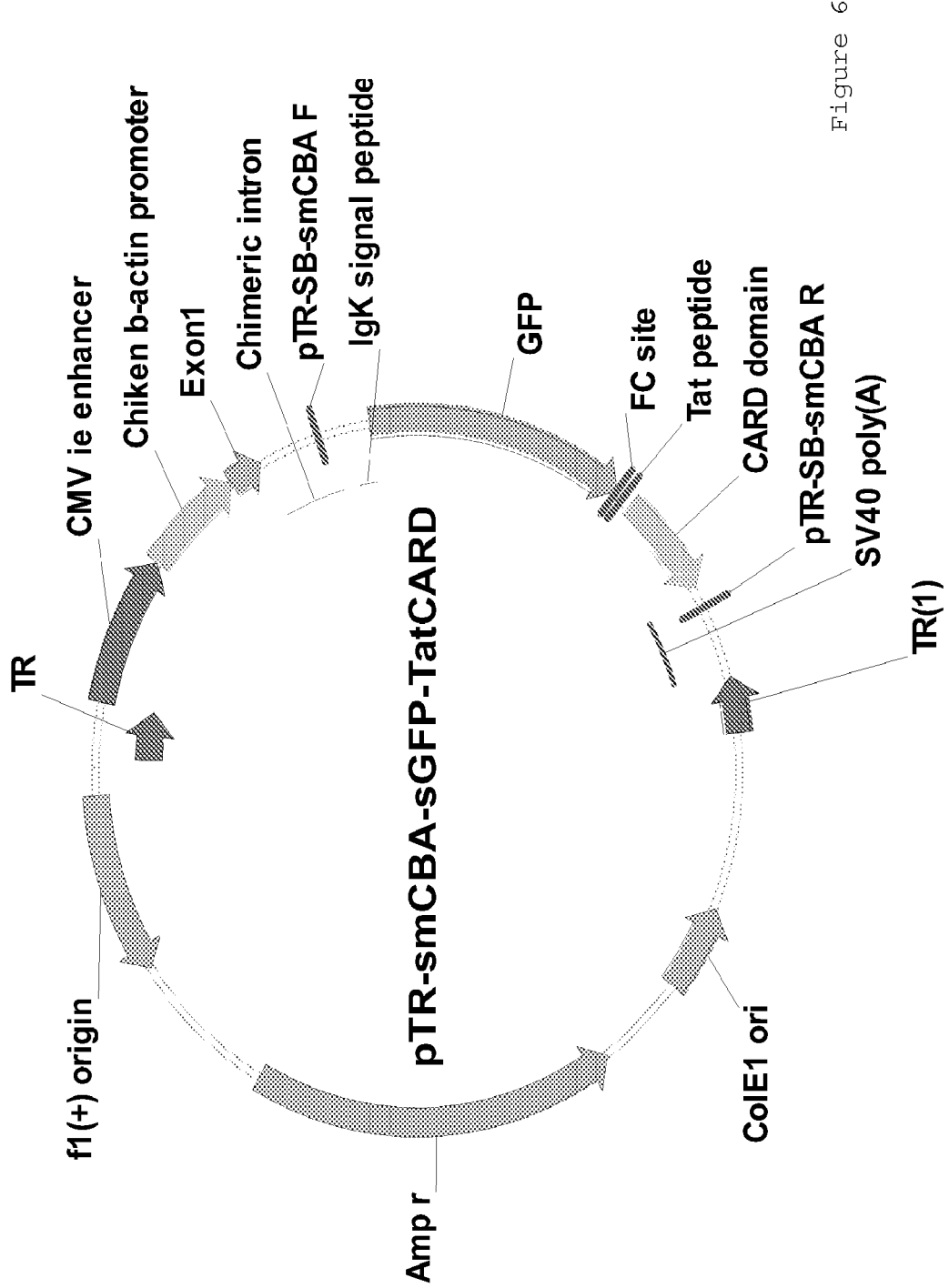

FIG. 6. Development of an AAV vector delivering a secretable form of the TatCARD fused protein. The fused protein TatCARD DNA sequence was cloned in frame and downstream of the IgK signal peptide and GFP gene in a puc57 plasmid. The new construct IgK signal peptide-GFP-FC-TatCARD was then cloned in an AAV plasmid. This plasmid contains the chicken-beta actin (smCBA) promoter flanked by the terminal repeats (TRs) sequences of the AAV virus. The IgK signal peptide fused to the GFP allows this gene to be targeted for secretion upon translation. This secreted GFP (sGFP) is, in-turn, linked to the TatCARD fused protein by a furin cleavage (FC) site which allows the cleavage and separation of sGFP from the TatCARD upon cleavage at the cell membrane by the furin enzyme. Overall, this vector will deliver a secretable form of the fused TatCARD protein.

Figure 7A:
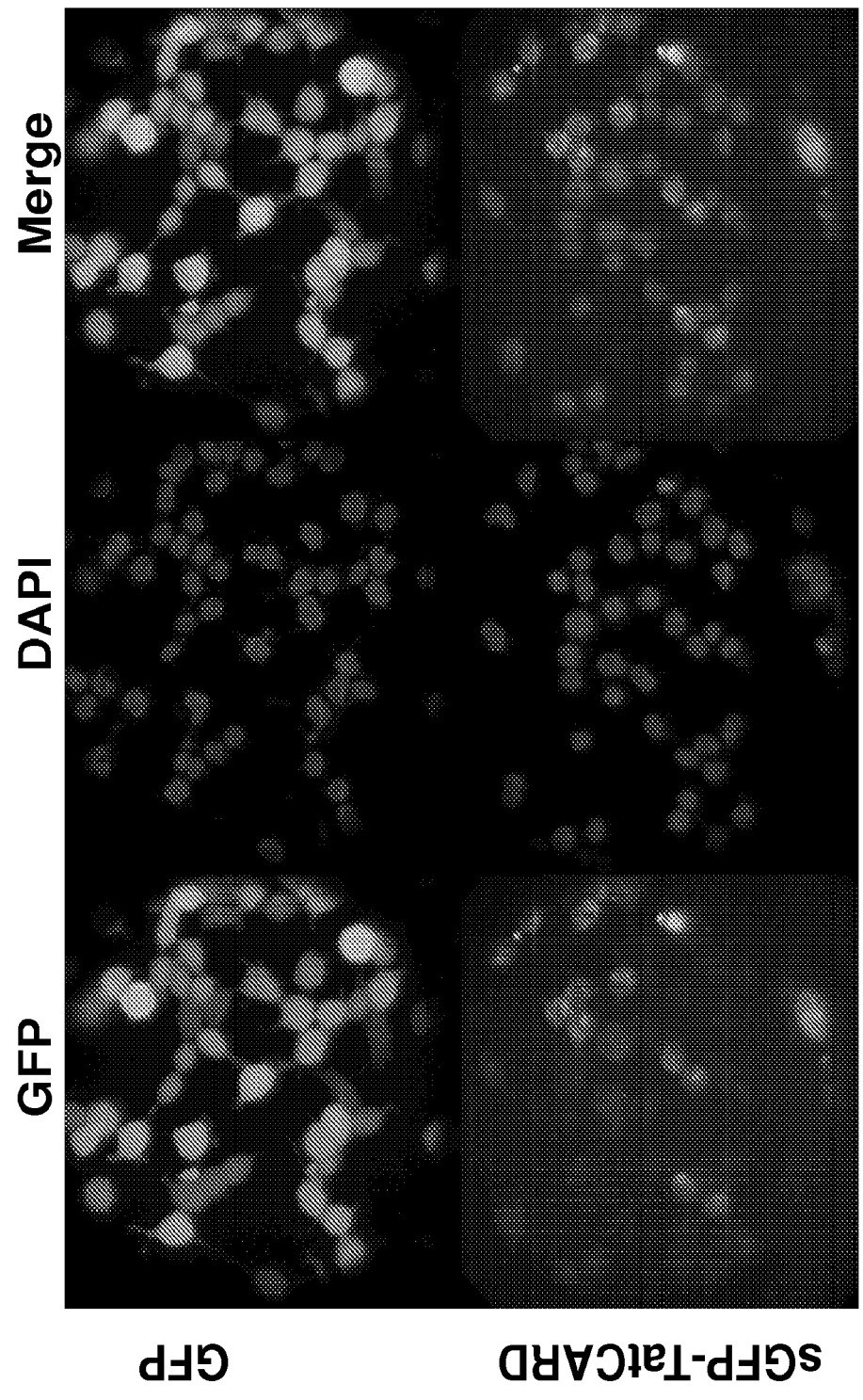

FIG. 7a. The sGFP-TatCARD protein construct has a punctate pattern in vitro. HEK293T cells were transfected with either pTR-smCBA-GFP or pTR-smCBA-sGFP-TatCARD. Cells were imaged 48 hours post-transfection using fluorescence microscopy to determine the distribution of GFP in both cell groups. Cells transfected with the GFP plasmid showed a typical cytoplasmic distribution of GFP, whereas the cells transfected with the sGFP-TatCARD plasmid showed a distinct punctate pattern characteristic of molecules that are actively being targeted for cell secretion.

Figure 7B:
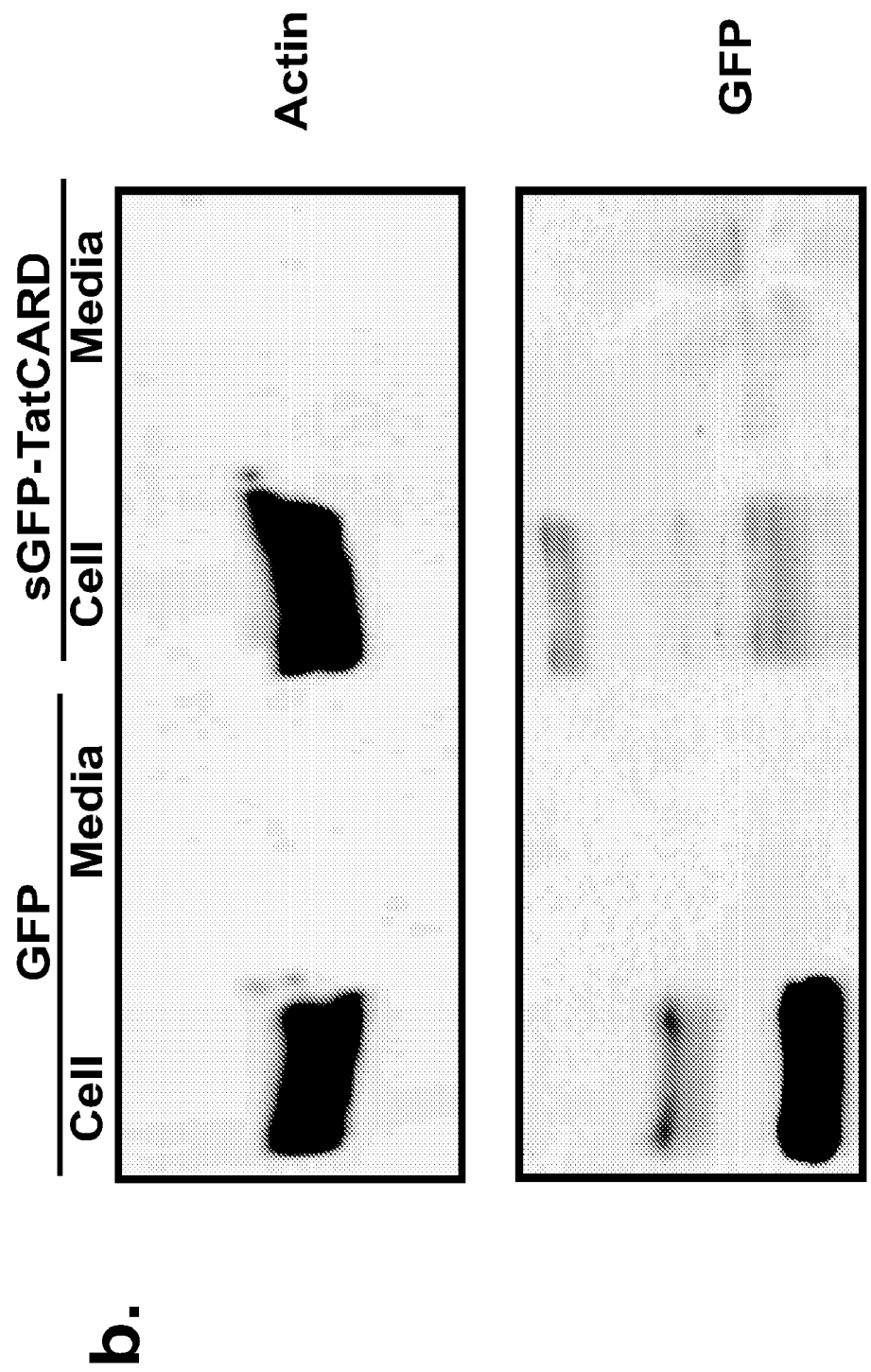

FIG. 7b. Detection of GFP in the media of cells transfected with the pTR-smCBA-sGFP-TatCARD plasmid. Transfected HEK293T cells were lysed at 48 hours post-transfection after imaging, and their conditioned media harvested. Cells were lysed for protein extraction as done previously. Their corresponding conditioned media was concentrated sequentially using a 50 KDa concentrator and collecting the eluted fraction. This fraction was then subjected to a second concentration step by using a 3 KDa concentrator. The concentrated media containing molecules smaller than 50 KDa but larger than 3 KDa was prepared for SDS-PAGE. Cell lysate (Cell, 30 microg. per lane) and concentrated media (Media, 15 microg. per lane) were separated in a 12% SDS-PAGE. The presence of GFP was determined by western blot with an anti-GFP antibody. To bands of equal intensity were observed in the cell lysate of sGFP-TatCARD corresponding to the sGFP-TatCARD and the sGFP products. One band of approximately the same size of the GFP was observed in the media of sGFP-TatCARD, thus suggesting the secretion and cleavage of the sGFP-TatCARD construct. Actin was used as a loading control.

Figure 8:
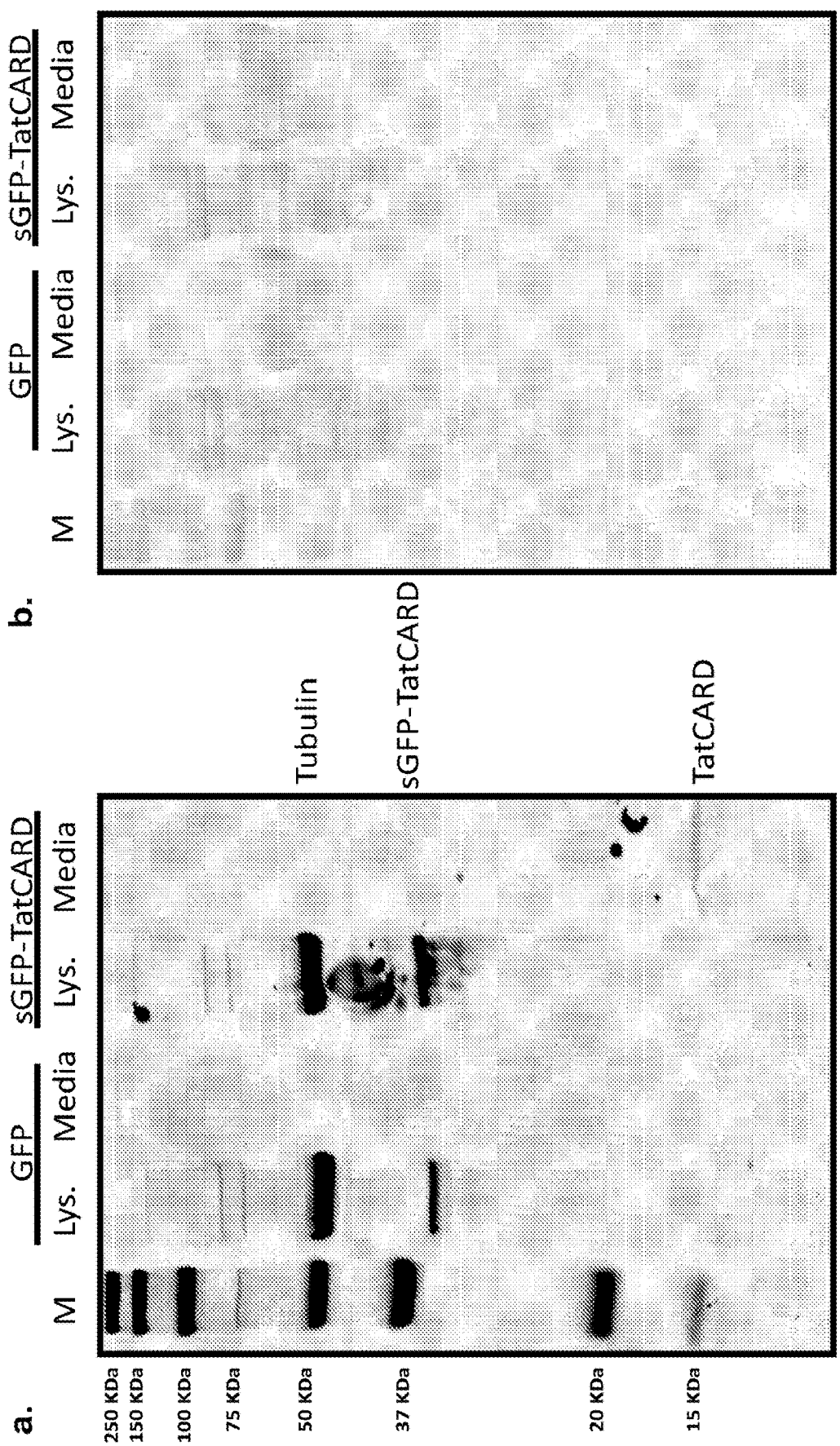

FIG. 8. In vitro testing of the AAV1/smCBA-sGFP-TatCARD vector a HEK293T were transduced with 10,000 vgc/cell of either AAV1/smCBA-GFP or AAV1/smCBA-sGFP-TatCARD. Growth media was replaced with 2 mL of low-protein media 48 hrs after transduction. Conditioned media and cells were harvested 72 hrs after transduction. Protein was extracted from cell lysates as done in previous experiments. Conditioned media was concentrated using a 3 KDa column by centrifugation. Using a 12% SDS-PAGE, samples were separated using 30 microg. of each lysate (lys.) and 20 microg. of each conditioned media (media). The presence of TatCARD fused protein was determined by western blot using an anti-ASC antibody that recognizes the CARD domain of the ASC protein. Two bands were detected only in the media of cells transduced with AAV1/smCBA-sGFP-TatCARD corresponding to the fused sGFP-TatCARD (~37 KDa) and the cleaved TatCARD products (~15 KDa). Tubulin detection was used as a loading control for cell lysate samples b. Amido black staining of PVDF membrane showing total protein loaded in each lane of the gel.

Figure 9:
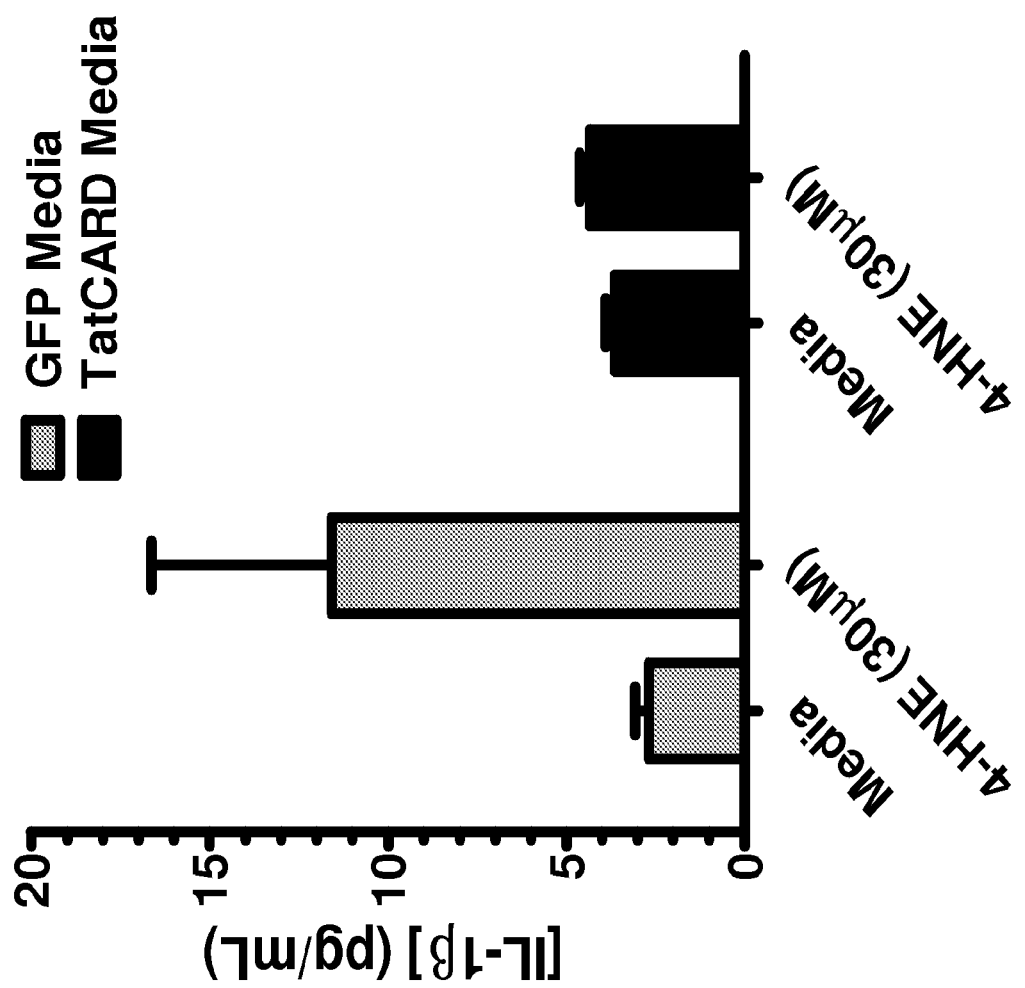

FIG. 9. The biological activity of TatCARD can be transferred in vitro. Conditioned media from cells transfected with either GFP or TatCARD expressing plasmid was overlayed on wild type ARPE-19 cells. These cells were then stimulated with 4HNE and the concentration of secreted IL-1β in the media was measured by ELISA.

Figure 10A:
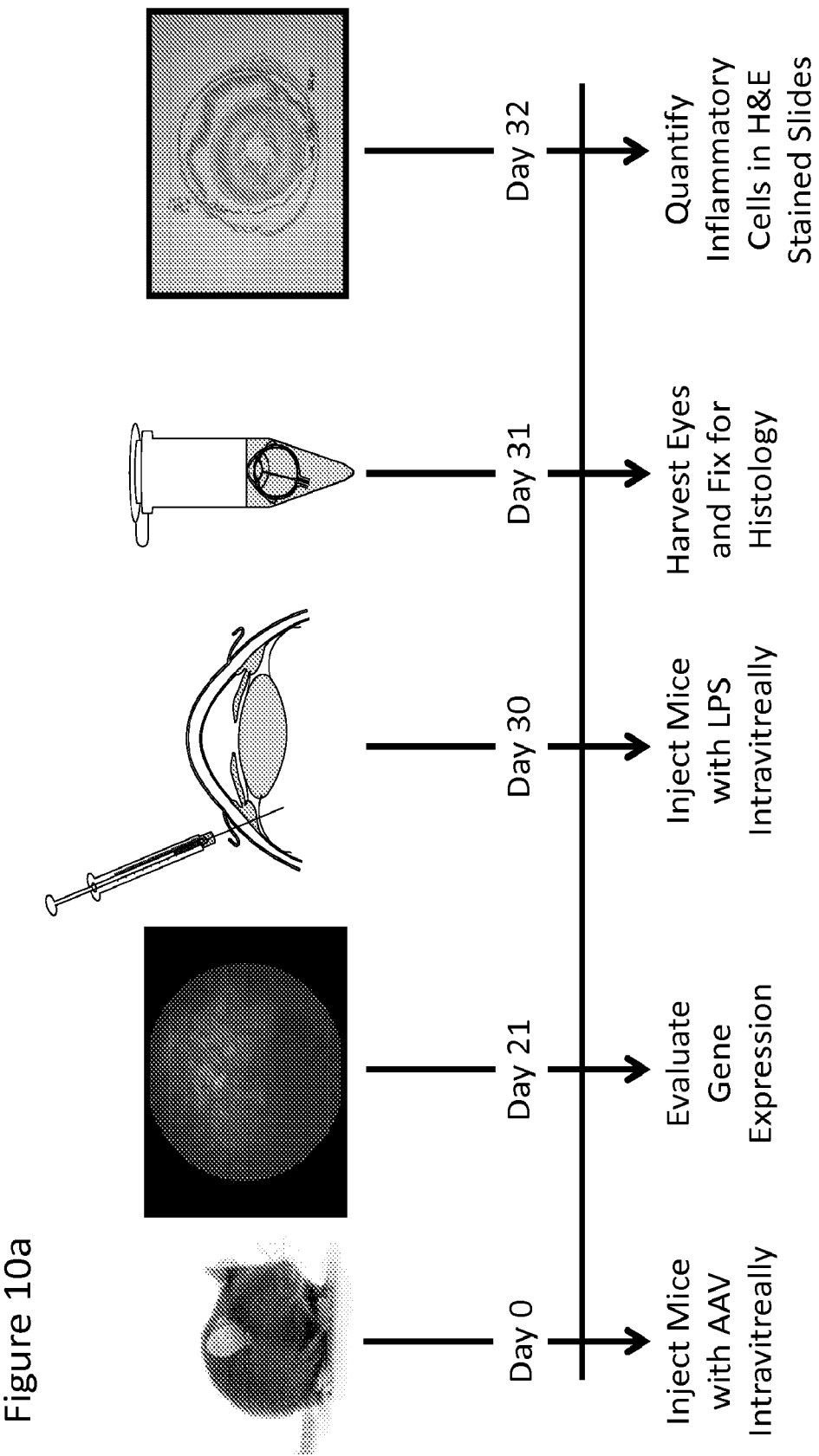

FIG. 10a. Experimental design for testing the AAV2-QUAD-T419V/smCBA-sGFP-TatCARD vector in the endotoxin-induced mouse model. C57BL6J mice were injected intravitreally with $3 \times 10^9$ vector genomes delivering either GFP or TatCARD AAV2. Twenty days later gene expression was determined by fluorescent fundoscopy. Nine days afterwards mice received 25 ng of LPS intravitreally. Eyes were enucleated 24 hours later and fixed for histological analysis. Infiltrative cells were then quantified by two individuals.

Figure 10B:
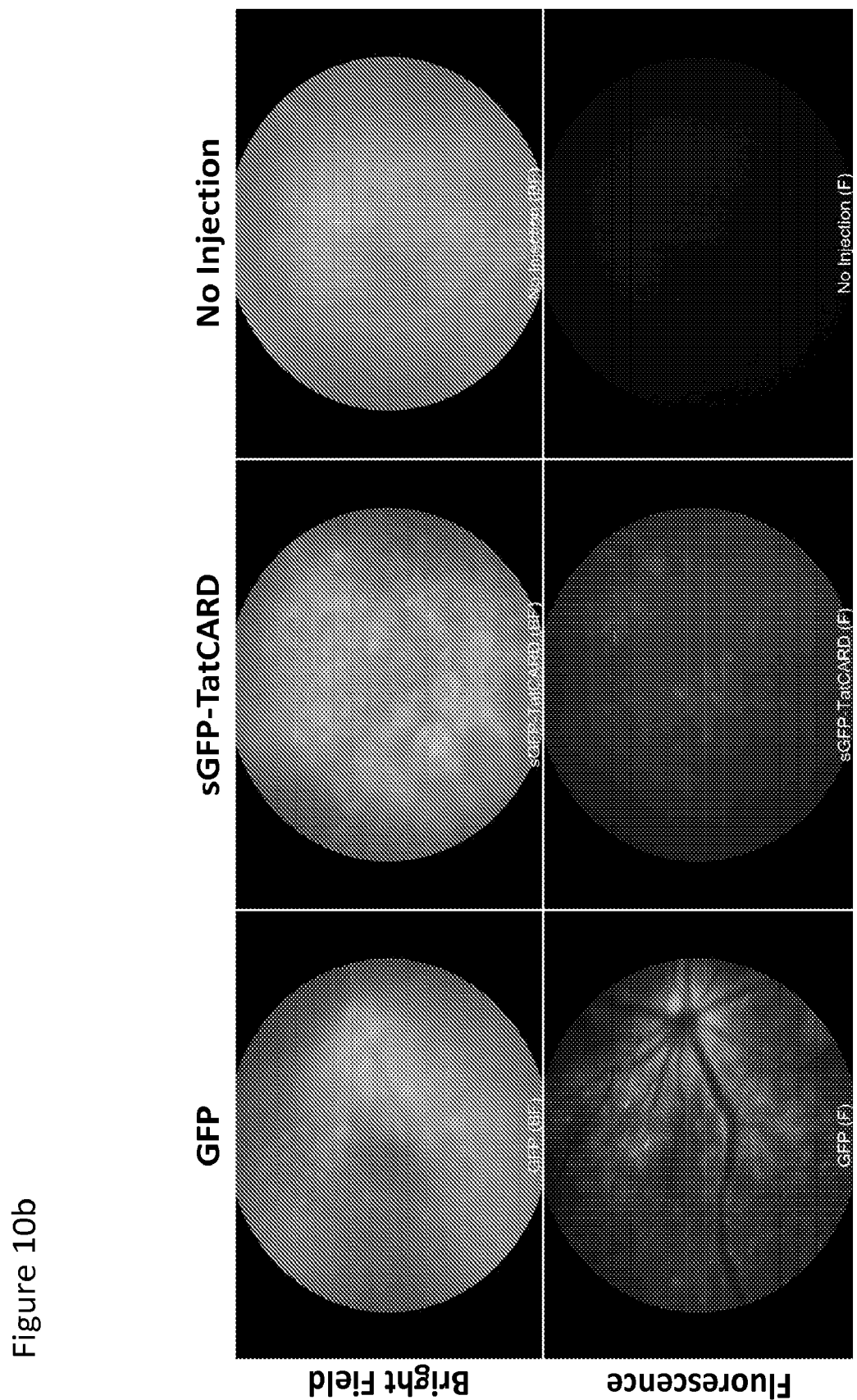

FIG. 10b. Fundus of animals injected with AAV vector. Mice were evaluated 21 days after AAV injection by fluorescent fundoscopy. Eyes expressing GFP showed a expression of GFP in individual cells. Eyes injected with the sGFP-TatCARD delivering AAV vector showed a diffused GFP expression representative of secreted GFP. Non-injected eye was used as a negative control.

Figure 10C:
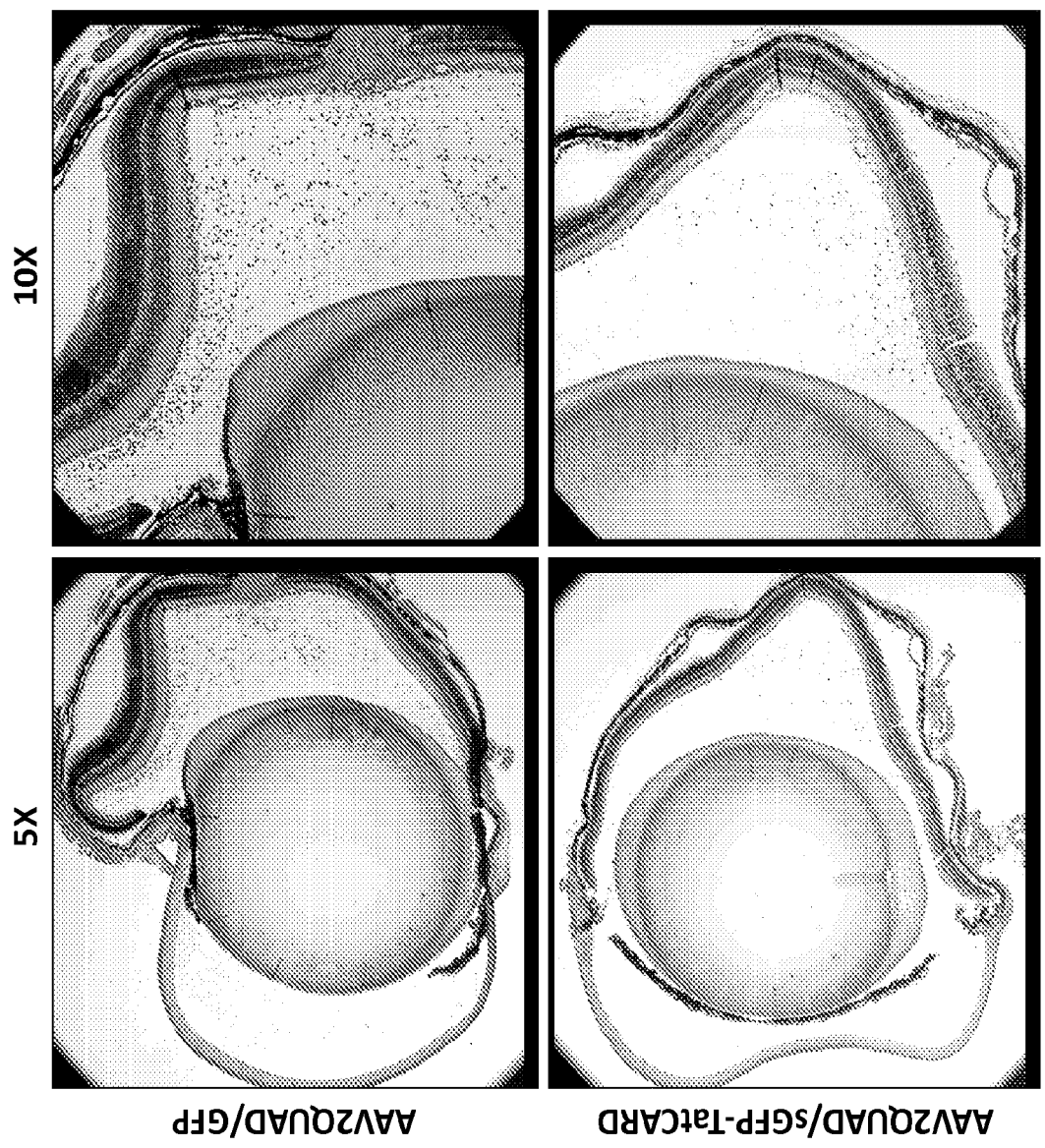

FIG. 10c. Representative histological differences between eyes injected with GFP and eyes injected with sGFP-TatCARD. Histological sections of eyes injected with AAV vector delivering either GFP or sGFP-TatCARD. Bright field pictures were taken at 5× and 10× (original magnification) to demonstrate the presence of infiltrative cells within the vitreous body.

Figure 10D:
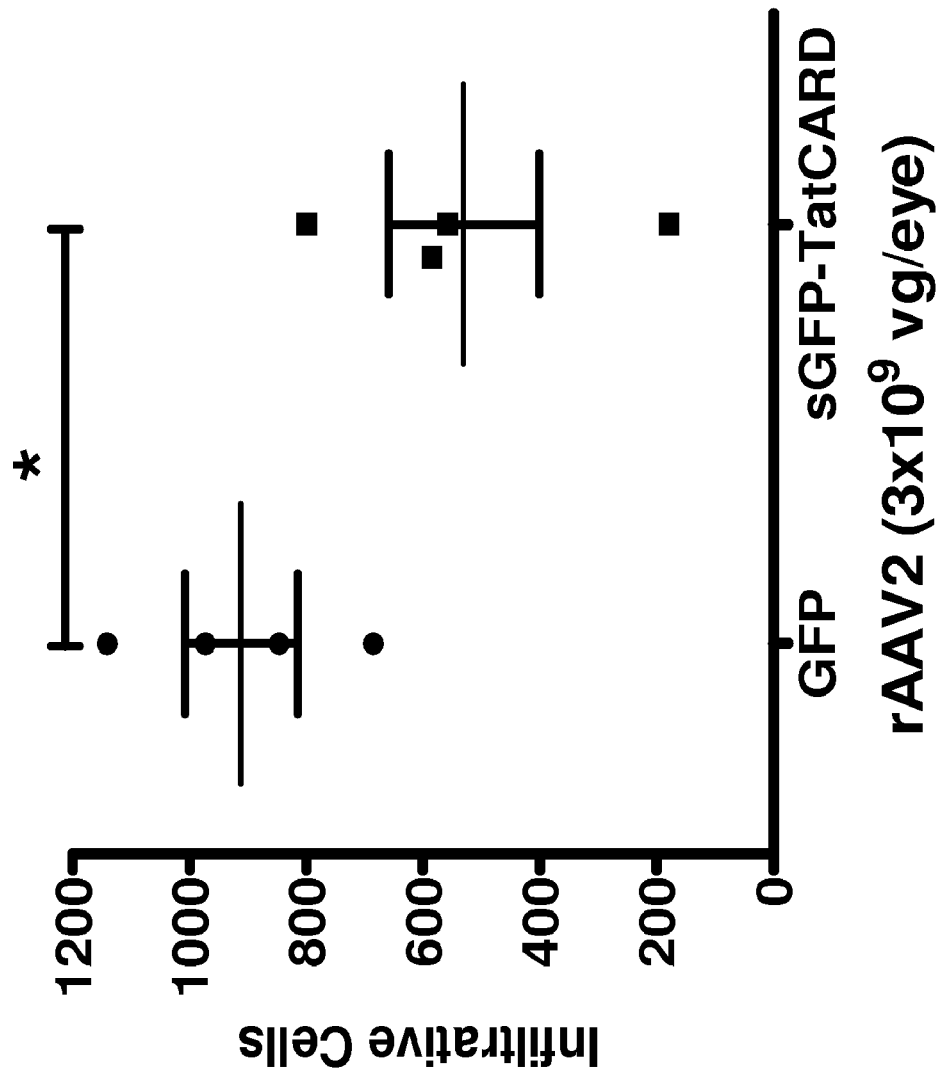

FIG. 10d. Expression of the TatCARD gene product decreases the number of infiltrating cells in the EIU mouse model. Infiltrative cells within the vitreous body were quantified by two individuals. Average values were compared using the student t-test for paired observations. There is statistically significant decrease in the number of infiltrative cells in eyes injected with the AAV vector delivering the sGFP-TatCARD gene.

DETAILED DESCRIPTION

Definitions

"Agent" as used herein pertains to a CARD polypeptide or a CARD nucleotide that encodes a CARD polypeptide. Unless otherwise indicated, an agent may include a delivery vehicle that comprises a CARD nucleotide for expression of a CARD polypeptide.

"Biocompatible" refers to a material that is substantially non-toxic to cells in vitro, e.g., if its addition to cells in culture results in less than or equal to 20% cell death. A material is considered biocompatible with respect to a recipient if it is substantially nontoxic to the recipient's cells in the quantities and at the location used, and also does not elicit or cause a significant deleterious or untoward effect on the recipient's body, e.g., an immunological or inflammatory reaction, unacceptable scar tissue formation, etc.

"Biodegradable" means that a material is capable of being broken down physically and/or chemically within cells or within the body of a subject, e.g., by hydrolysis under physiological conditions, by natural biological processes such as the action of enzymes present within cells or within the body, etc., to form smaller chemical species which can be metabolized and, optionally, reused, and/or excreted or otherwise disposed of. Preferably a biodegradable compound is biocompatible.

"Concurrent administration" as used herein with respect to two or more agents, e.g., therapeutic agents, is administration performed using doses and time intervals such that the administered agents are present together within the body, or at a site of action in the body such as within the eye) over a time interval in less than de minimis quantities, i.e., in quantities sufficient to have a detectable biological effect or response. The time interval can be minutes, hours, days, weeks, etc. Accordingly, the agents may, but need not be, administered together as part of a single composition. In addition, the agents may, but need not be, administered simultaneously (e.g., within less than 5 minutes, or within less than 1 minute) or within a short time of one another (e.g., less than 1 hour, less than 30 minutes, less than 10 minutes, approximately 5 minutes apart). According to various embodiments of the invention agents administered within such time intervals may be considered to be administered at substantially the same time. One of ordinary skill in the art will be able to readily determine appropriate doses and time interval between administration of the agents so that they will each be present at more than de minimis levels within the body or, preferably, at effective concentrations within the body. When administered concurrently, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

An "effective amount" of an active agent refers to the amount of the active agent sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, for diseases or conditions involving the eye, an effective amount may be an amount sufficient to achieve one or more of the following: (i) prevent drusen formation; (ii) cause a reduction in drusen number and/or size (drusen regression); (iii) cause a reduction in or prevent lipofuscin deposits; (iv) prevent visual loss or slow the rate of visual loss; (v) prevent or slow the rate of choroidal neovascularization; (vi) cause a reduction in size and/or number of lesions characterized by choroidal neovascularization; (vii) improve visual acuity and/or contrast sensitivity; (viii) prevent or reduce the rate of photoreceptor or RPE cell atrophy or apoptosis; (ix) prevent or slow progression from the wet to the dry form of AMD.

"Local administration" or "local delivery", in reference to delivery of a composition, formulation, or device of the invention, refers to delivery that does not rely upon transport of the agent to its intended target tissue via the vascular or lymphatic system from a site of administration that is remote from the intended target tissue. The agent is delivered directly to its intended target tissue or in the vicinity thereof, e.g. by injection or implantation. It will be appreciated that a small amount of the delivered agent may enter the vascular system and may ultimately reach the target tissue via the vascular system.

"Macular degeneration related condition" refers to any of a number of disorders and conditions in which the macula degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and capillary endothelial cells. AMD is the major macular degeneration related condition, but a number of others are known including, but not limited to, Best macular dystrophy, Sorsby fundus dystrophy, Mallatia Leventinese and Doyne honeycomb retinal dystrophy.

"Ocular device" refers to a drug delivery device that has appropriate structure, dimensions, shape, and/or configuration and is made of appropriate materials so that it may be placed in or on the surface of the eye without causing unacceptable interference with the physiology or functioning of the eye. Preferably placement of an ocular device does not significantly disrupt vision. An ocular device is typically a solid or semi-solid article of manufacture and is typically macroscopic, i.e., visible with the naked eye.

"Ocular neovascularization" (ONV) is used herein to refer to choroidal neovascularization or retinal neovascularization, or both.

"Polypeptide", as used herein, refers to a polymer of amino acids and/or amino acid analogs which may or may not be modified. Various amino acid analogs and modifications are described herein. A polypeptide may be cyclic or linear and may be branched or unbranched. The term "amino acid sequence" or "polypeptide sequence" as used herein can refer to the polypeptide material itself and is not restricted to the sequence information (i.e. the succession of letters or three letter codes chosen among the letters and codes used as abbreviations for amino acid names) that biochemically characterizes a polypeptide. For purposes of the disclosure the use of the term "polypeptide" and "protein" are interchangeable unless specifically noted otherwise.

"Purified", as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

"Retinal neovascularization" (RNV) refers to the abnormal development, proliferation, and/or growth of retinal blood vessels, e.g., on the retinal surface.

"Sequential administration" of two or more agents refers to administration of two or more agents to a subject such that the agents are not present together in the subject's body at greater than de minimis concentrations. Administration of the agents may, but need not, alternate. Each agent may be administered multiple times.

"Subject", as used herein, refers to an individual to whom an agent is to be delivered, e.g., for experimental, diagnostic, and/or therapeutic purposes. Preferred subjects are mammals, particularly domesticated mammals (e.g., dogs, cats, etc.), primates, or humans.

"Significant sequence homology" as applied to an amino acid sequence means that the sequence displays at least approximately 20% identical or conservatively replaced amino acids, preferably at least approximately 30%, at least approximately 40%, at least approximately 50%, at least approximately 60% identical or conservatively replaced amino acids, desirably at least approximately 70% identical or conservatively replaced amino acids, more desirably at least approximately 80% identical or conservatively replaced amino acids, and most desirably at least approximately 90% amino acid identical or conservatively replaced amino acids relative to a reference sequence. When two or more sequences are compared, any of them may be considered the reference sequence. % identity can be calculated using a FASTA or BLASTP algorithm, using default parameters. A PAM250 or BLOSUM62 matrix may be used. For purposes of calculating % identical or conservatively replaced residues, a conservatively replaced residue is considered identical to the residue it replaces. Conservative replacements may be defined in accordance with Stryer, L,

*Biochemistry*, 3rd ed., 1988, according to which amino acids in the following groups possess similar features with respect to side chain properties such as charge, hydrophobicity, aromaticity, etc. (1) Aliphatic side chains: G, A, V, L, I; (2) Aromatic side chains: F, Y, W; (3) Sulfur-containing side chains: C, M; (4) Aliphatic hydroxyl side chains: S, T; (5) Basic side chains: K, R, H; (6) Acidic amino acids: D, E, N, Q; (7) Cyclic aliphatic side chain: P "Substantial sequence homology" as applied to a sequence means that the sequence displays at least approximately 60% identity, desirably at least approximately 70% identity, more desirably at least approximately 80% identity, and most desirably at least approximately 90% identity relative to a reference sequence. When two or more sequences are compared, any of them may be considered the reference sequence. % identity can be calculated using a FASTA, BLASTN, or BLASTP algorithm, depending on whether amino acid or nucleotide sequences are being compared. Default parameters may be used. A PAM250 or BLOSUM62 matrix may be used.

A "sustained release formulation" is a composition of matter that comprises a therapeutic agent as one of its components and further comprises one or more additional components, elements, or structures effective to provide sustained release of the therapeutic agent, optionally in part as a consequence of the physical structure of the formulation. Sustained release is release or delivery that occurs either continuously or intermittently over a period of time e.g., at least 1, 2, 4, or 6 weeks, at least 1, 2, 3, 4, 6, 8, 10, 12, 15, 18, or 24 months, or longer.

"Treating" or "treatment of" as used herein, refers to providing any type of medical or surgical management to a subject. Treating can include, but is not limited to, administering a composition comprising a therapeutic agent to a subject. "Treating" includes any administration or application of a agent or composition of the invention to a subject for purposes such as curing, reversing, alleviating, reducing the severity of, inhibiting the progression of, or reducing the likelihood of a disease, disorder, or condition or one or more symptoms or manifestations of a disease, disorder or condition. In a specific example, a composition of this invention can be administered to a subject who has developed a macular degeneration related condition risk of developing an infection relative to a member of the general population. A composition of this invention can be administered to a subject who has developed an eye disorder such as exudative or non-exudative AMD or diabetic retinopathy or is at increased risk or who has exhibited symptoms of developing such a disorder relative to a member of the general population. A composition of this invention can be administered prophylactically, i.e., before development of any symptom or manifestation of the condition. Typically in this case the subject will be at risk of developing the condition. Treating also may comprise treating a subject exhibiting symptoms of a certain disease or condition.

A variety of factors including oxidative stress, inflammation with a possible autoimmune component, genetic background (e.g., mutations), and environmental or behavioral features such as smoking and diet may contribute to the pathogenesis of AMD in manners that are as yet poorly understood (Zarbin, M A, *Arch Opthalmol.* 122:598-614, 2004). Regardless of the underlying etiology, the clinical hallmark of AMD is the appearance of drusen, localized deposits of lipoproteinaceous material that accumulate in the space between the RPE and Bruch's membrane, which separates the RPE from the choroidal vessels (choriocapillaris). Drusen are typically the earliest clinical finding in AMD. The existence of macular drusen is a strong risk factor for the development of both wet and dry forms of AMD (Ambati, J., et al., *Surv. Opthalmol.*, 48(3): 257-293, 2003).

Ocular inflammation can affect a large number of eye structures including the conjunctiva, cornea, episclera, sclera, uveal tract, retina, vasculature, optic nerve, and orbit. Evidence of ocular inflammation can include the presence of inflammation-associated cells such as white blood cells (e.g., neutrophils, macrophages) in the eye, the presence of endogenous inflammatory mediators known in the art, one or more symptoms such as eye pain, redness, light sensitivity, blurred vision and floaters, etc. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis and choroiditis. Uveitis can arise from a number of different causes and is associated with a number of different diseases, including, but not limited to, rheumatic diseases such as rheumatic diseases (e.g., ankylosing spondylitis and juvenile rheumatoid arthritis), certain infectious diseases such as tuberculosis and syphilis, other conditions such as sarcoidosis, systemic lupus erythematosus, chemical injury, trauma, surgery, etc. Keratis refers to inflammation of the cornea. Keratitis has a diverse array of causes including bacterial, viral, or fungal infection, trauma, and allergic reaction. Amoebic infection of the cornea, e.g., caused by Acanthamoeba, is a particular problem for contact lens wearers. Scleritis refers to inflammation of the sclera. Uveitis, keratitis, and scleritis, and methods for their diagnosis are well known in the art. Symptoms of the various inflammatory conditions that affect the eye can include, but are not limited to, eye pain, redness, light sensitivity, tearing, blurred vision, floaters. Ocular inflammation of various types is well known to occur in association with a variety of local or systemic diseases, some of which are noted above. In some instances the cause may remain unknown.

DETAILED DESCRIPTION

According to one embodiment, provided is a method for the prevention, amelioration, or treatment of a disease or condition associated with oxidative stress or inflammation in a subject comprising administration of a therapeutically effective amount of an agent to the subject, wherein the agent is a CARD protein. In a specific embodiment, the CARD protein is a TatCARD protein, or a polypeptide having substantial sequence homology therewith.

In a specific embodiment, provided is a method of preventing, ameliorating or treating retinal and RPE inflammation that involves administration of a CARD protein. In a more specific embodiment, the CARD protein is secreted from cells transfected with an AAV vector engineered to express CARD, and in particular TatCARD.

In another embodiment, provided is a viral vector engineered to express TatCARD. In specific embodiments, the viral vector is an AAV plasmid or a lentiviral plasmid.

In a further embodiment, provided are cells stably transfected with a nucleotide sequence encoding a CARD protein. In a specific embodiment, the CARD protein is TatCARD.

In a particular embodiment, the invention pertains to a method of treating a disease associated with inflammation or oxidative stress involving the eye. Specific examples of such diseases include but are not limited to macular degeneration, age-related macular degeneration (AMD), geographic atrophy, wet AMD, dry AMD, drusen formation, dry eye, diabetic retinopathy, vitreoretinopathy, corneal inflammation, uveitis, ocular hypertension or glaucoma.

Vectors

In some embodiments, viral vectors are used to transfect cells with a CARD expression construct. In a particular embodiment, adeno-associated viral vectors are used. Other vectors of the invention used in vitro, in vivo, and ex vivo include viral vectors, such as retroviruses (including lentiviruses), herpes viruses, alphavirus, adenovirus, vaccinia virus, papillomavirus, or Epstein Barr virus (EBV).

Methods for constructing and using viral vectors are known in the art (see, e.g., Miller and Rosman, BioTechniques 1992, 7:980-990). In accordance with the present invention there may be employed conventional molecular biology, microbiology, and recombinant DNA techniques within the skill of the art. Such techniques are well-known and are explained fully in the literature. See, e.g., Sambrook, Fritsch and Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors) and Origene (Rockville, Md.).

In certain embodiments, the viral vectors of the invention are replication defective, that is, they are unable to replicate autonomously in the target cell. Preferably, the replication defective virus is a minimal virus, i.e., it retains only the sequences of its genome which are necessary for target cell recognition and encapsidating the viral genome. Replication defective virus is not infective after introduction into a cell. Use of replication defective viral vectors allows for administration to cells in a specific, localized area, without concern that the vector can infect other cells. Thus, a specific tissue can be specifically targeted. Examples of particular vectors include, but are not limited to, defective herpes virus vectors (see, e.g., Kaplitt et al., Molec. Cell. Neurosci. 1991, 2:320-330; Patent Publication RD 371005 A; PCT Publications No. WO 94/21807 and WO 92/05263), defective adenovirus vectors (see, e.g., Stratford-Perricaudet et al., J. Clin. Invest. 1992, 90:626-630; La Salle et al., Science 1993, 259:988-990; PCT Publications No. WO 94/26914, WO 95/02697, WO 94/28938, WO 94/28152, WO 94/12649, WO 95/02697, and WO 96/22378), and defective adeno-associated virus vectors (Samulski et al., J. Virol. 1987, 61:3096-3101; Samulski et al., J. Virol. 1989, 63:3822-3828; Lebkowski et al., Mol. Cell. Biol. 1988, 8:3988-3996; PCT Publications No. WO 91/18088 and WO 93/09239; U.S. Pat. Nos. 4,797,368 and 5,139,941; European Publication No. EP 488 528).

Adeno-associated virus-based vectors. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see PCT Publications No. WO 91/18088 and WO 93/09239; U.S. Pat. Nos. 4,797,368 and 5,139,941; EP Publication No. 488 528). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (e.g., an adenovirus). The AAV recombinants which are produced are then purified by standard techniques.

Adenovirus-based vectors. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see PCT Publication No. WO94/26914). Those adenoviruses of animal origin which can be used within the scope of the present invention include adenoviruses of canine, bovine, murine (e.g., Mav1 [Beard et al., Virology, 1990, 75:81]), ovine, porcine, avian, and simian (e.g., SAV) origin. Preferably, the adenovirus of animal origin is a canine adenovirus, more preferably a CAV2 adenovirus (e.g., Manhattan or A26/61 strain [ATCC Accession No. VR-800]). Various replication defective adenovirus and minimum adenovirus vectors have been described (PCT Publications No. WO94/26914, WO95/02697, WO94/28938, WO94/28152, WO94/12649, WO95/02697, WO96/22378). The replication defective recombinant adenoviruses according to the invention can be prepared by any technique known to the person skilled in the art (Levrero et al., Gene, 1991, 101:195; EP Publication No. 185 573; Graham, EMBO J., 1984, 3:2917; Graham et al., J. Gen. Virol., 1977, 36:59). Recombinant adenoviruses are recovered and purified using standard molecular biological techniques, which are well known to one of ordinary skill in the art.

Retroviral vectors. In another embodiment, the invention provides retroviral vectors, e.g., as described in Mann et al., Cell 1983, 33:153; U.S. Pat. Nos. 4,650,764, 4,980,289, 5,124,263, and 5,399,346; Markowitz et al., J. Virol. 1988, 62:1120; EP Publications No. 453 242 and 178 220; Bernstein et al. Genet. Eng. 1985, 7:235; McCormick, BioTechnology 1985, 3:689; and Kuo et al., 1993, Blood, 82:845. The retroviruses are integrating viruses which infect dividing cells. The retrovirus genome includes two LTRs, an encapsidation sequence and three coding regions (gag, pol and env). Replication defective non-infectious retroviral vectors are manipulated to destroy the viral packaging signal, but retain the structural genes required to package the co-introduced virus engineered to contain the heterologous gene and the packaging signals. Thus, in recombinant replication defective retroviral vectors, the gag, pol and env genes are generally deleted, in whole or in part, and replaced with a heterologous nucleic acid sequence of interest. These vectors can be constructed from different types of retroviruses, such as HIV (human immuno-deficiency virus), MoMuLV (murine Moloney leukaemia virus), MSV (murine Moloney sarcoma virus), HaSV (Harvey sarcoma virus), SNV (spleen necrosis virus), RSV (Rous sarcoma virus), and Friend virus. Suitable packaging cell lines have been described in the prior art, in particular, the cell line PA317 (U.S. Pat. No. 4,861,719); the PsiCRIP cell line (PCT Publication No. WO 90/02806) and the GP+envAm-12 cell line (PCT Publication No. WO 89/07150). In addition, recombinant retroviral vectors can contain modifications within the LTRs for suppressing transcriptional activity as well as extensive encapsidation sequences which may include a part of the gag gene (Bender et al., J. Virol. 1987, 61:1639). Recombinant retroviral vectors are purified by standard techniques known to those having ordinary skill in the art.

Retrovirus vectors can also be introduced by DNA viruses, which permits one cycle of retroviral replication and amplifies transfection efficiency (see PCT Publications No. WO 95/22617, WO 95/26411, WO 96/39036, WO 97/19182).

In a specific embodiment of the invention, lentiviral vectors can be used as agents for the direct delivery and sustained expression of a transgene in several tissue types, including brain, retina, muscle, liver, and blood. This subtype of retroviral vectors can efficiently transduce dividing and nondividing cells in these tissues, and maintain long-term expression of the gene of interest (for a review, see, Naldini, Curr. Opin. Biotechnol. 1998, 9:457-63; Zufferey, et al., J. Virol. 1998, 72:9873-80). Lentiviral packaging cell lines are available and known generally in the art (see, e.g., Kafri, et al., J. Virol., 1999, 73: 576-584).

Non-viral vectors. In another embodiment, the invention provides non-viral vectors that can be introduced in vivo, provided that these vectors contain a targeting peptide, protein, antibody, etc. that specifically binds HALR. For example, compositions of synthetic cationic lipids, which can be used to prepare liposomes for in vivo transfection of a vector carrying an anti-tumor therapeutic gene, are described in Feigner et. al., Proc. Natl. Acad. Sci. USA 1987, 84:7413-7417; Feigner and Ringold, Science 1989, 337: 387-388; Mackey, et al., Proc. Natl. Acad. Sci. USA 1988, 85:8027-8031; and Ulmer et al, Science 1993, 259:1745-1748. Useful lipid compounds and compositions for transfer of nucleic acids are described, e.g., in PCT Publications No. WO 95/18863 and WO96/17823, and in U.S. Pat. No. 5,459,127. Targeting peptides, e.g., laminin or HALR-binding laminin peptides, and proteins such as anti-HALR antibodies, or non-peptide molecules can be coupled to liposomes covalently (e.g., by conjugation of the peptide to a phospholipid or cholesterol; see also Mackey et al., supra) or non-covalently (e.g., by insertion via a membrane binding domain or moiety into the bilayer membrane).

Alphaviruses are well known in the art, and include without limitation Equine Encephalitis viruses, Semliki Forest virus and related species, Sindbis virus, and recombinant or ungrouped species (see Strauss and Strauss, Microbiol. Rev. 1994, 58:491-562, Table 1, p. 493).

As used herein the term "replication deficient virus" has its ordinary meaning, i.e., a virus that is propagation incompetent as a result of modifications to its genome. Thus, once such recombinant virus infects a cell, the only course it can follow is to express any viral and heterologous protein contained in its genome. In a specific embodiment, the replication defective vectors of the invention may contain genes encoding nonstructural proteins, and are self-sufficient for RNA transcription and gene expression. However, these vectors lack genes encoding structural proteins, so that a helper genome is needed to allow them to be packaged into infectious particles. In addition to providing therapeutically safe vectors, the removal of the structural proteins increases the capacity of these vectors to incorporate more than 6 kb of heterologous sequences. In another embodiment, propagation incompetence of the adenovirus vectors of the invention is achieved indirectly, e.g., by removing the packaging signal which allows the structural proteins to be packaged in virions being released from the packaging cell line. As discussed above, viral vectors used to transfect cells and express CARD polypeptide may be used, and in a specific embodiment, the viral vectors involve a replication deficient virus.

Other Delivery Vehicles

Many nonviral techniques for the delivery of a nucleic acid sequence into a cell can be used, including direct naked DNA uptake (e.g., Wolff et al., Science 247: 1465-1468, 1990), receptor-mediated DNA uptake, e.g., using DNA coupled to asialoorosomucoid which is taken up by the asialoglycoprotein receptor in the liver (Wu and Wu, J. Biol. Chem. 262: 4429-4432, 1987; Wu et al., J. Biol. Chem. 266: 14338-14342, 1991), and liposome-mediated delivery (e.g., Kaneda et al., Expt. Cell Res. 173: 56-69, 1987; Kaneda et al., Science 243: 375-378, 1989; Zhu et al., Science 261: 209-211, 1993). Many of these physical methods can be combined with one another and with viral techniques; enhancement of receptor-mediated DNA uptake can be effected, for example, by combining its use with adenovirus (Curiel et al., Proc. Natl. Acad. Sci. USA 88: 8850-8854, 1991; Cristiana et al., Proc. Natl. Acad. Sci. USA 90: 2122-2126, 1993). Other examples include stem cells such as mesenchymal stem cells, hematopoietic stem cells, cardiac stem cells or neural stem cells, embryonic stem cells that have been engineered to express a sequence of interest.

Dosing, Delivery and Formulations

Further expounding on the definitions provided above, information regarding dosages and dosing is provided here.

Suitable dosage amounts and dosing regimens can be determined by the attending physician and may depend on the severity of the condition as well as the general age, health and weight of the patient to be treated.

Dosing may occur at intervals of minutes, hours, days, weeks, months or years or continuously over any one of these periods. Suitable dosages may lie within the range of about 0.1 ng per kg of body weight to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per body weight per dosage.

The agent of the invention may be administered in a single dose or a series of doses. While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The carrier must be pharmaceutically "acceptable" in the sense of being compatible with the other ingredients of the composition and not injurious to the patient. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

The methods of treatment described herein may involve administration of compositions comprising delivery vehicles, such as expression vectors, to the eye. Methods of treatment may also involve formulating CARD polypeptides into compositions for application to the eye of patients in need of therapy. Thus, such compositions are adapted for pharmaceutical use as an injectable agent, or as an eye drop or in contact lenses, inserts or the like, as described in greater detail below. Accordingly, formulation of compound into sterile water containing any desired diluents, salts, pH modifying materials and the like as are known to persons skilled in the pharmaceutical formulations art may be performed in order to achieve a solution compatible with administration to the eye. It may be that injectables, eye drops, inserts, contact lenses, gels and other liquid forms may require somewhat different formulations. All such formulations consistent with direct administration to the eye are comprehended hereby.

The compositions may also have antioxidants in ranges that vary depending on the kind of antioxidant used. The usage also depends on the amount of antioxidant needed to allow at least 2 years shelf-life for the pharmaceutical composition. One or more antioxidants may be included in the formulation. Certain commonly used antioxidants have maximum levels allowed by regulatory authorities. As such, the amount of antioxidant(s) to be administered should be enough to be effective while not causing any untoward effect. Such doses may be adjusted by a physician as needed, within the maximum levels set by regulatory authorities, and is well within the purview of the skilled artisan to determine the proper and effective dose. Reasonable ranges are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. N-Acetylcysteine may be present in a range of about 0.1% to about 5.0% weight by volume, with about 1% to about 10% of hydroxylamine concentration being preferred. Ascorbic acid or salt may also be present in a range of about 0.1% to about 5.0% weight by volume with about 1% to about 10% weight by volume of hydroxylamine concentration preferred. Other sulfhydryls, if included, may be the same range as for N-acetylcysteine. Other exemplary compounds include mercaptopropionyl glycine, N-acetyl cysteine, β-mercaptoethylamine, glutathione and similar species, although other anti-oxidant agents suitable for ocular administration, e.g., ascorbic acid and its salts or sulfite or sodium metabisulfite may also be employed.

A buffering agent may be used to maintain the pH of eye drop formulations in the range of about 4.0 to about 8.0; so as to minimize irritation of the eye. In certain embodiments, the pH is maintained at about 3.5 to about 6.0, preferably about 4.0 to about 5.5, in order to ensure that most of the hydroxylamine is in its protonated form for highest aqueous solubility. The buffer may be any weak acid and its conjugate base with a pKa of about 4.0 to about 5.5; e.g., acetic acid/sodium acetate; citric acid/sodium citrate. The pKa of the hydroxylamines is about 6.0. For direct intravitreal or intraocular injection, formulations should be at pH 7.2 to 7.5, preferably at pH 7.3-7.4.

The ophthalmologic compositions may also include tonicity agents suitable for administration to the eye. Among those suitable is sodium chloride to make formulations of the present invention approximately isotonic with 0.9% saline solution.

In certain embodiments, the compositions are formulated with viscosity enhancing agents. Exemplary agents are hydroxyethylcellulose, hydroxypropylcellulose, methylcellulose, and polyvinylpyrrolidone. The viscosity agents may be present in the compounds up to about 2.0% weight by volume. It may be preferred that the agents are present in a range from about 0.2% to about 0.5% weight by volume. A preferred range for polyvinylpyrrolidone may be from about 0.1% to about 2.0% weight by volume. One skilled in the art may prefer any range established as acceptable by the Food and Drug Administration.

The compounds used in accordance with the methods of the invention may have co-solvents added if needed. Suitable cosolvents may include glycerin, polyethylene glycol (PEG), polysorbate, propylene glycol, mannitol and polyvinyl alcohol. The presence of the co-solvents may exist in a range of about 0.2% to about 4.0% weight by volume. It may be preferred that mannitol may be formulated in the compounds of the invention in a range of about 0.5% to about 4.0% weight by volume. It may also be preferred that polyvinyl alcohol may be formulated in the compounds of the invention in a range of about 0.1% to about 4.0% weight by volume. One skilled in the art may prefer ranges established as acceptable by the Food and Drug Administration.

Preservatives may be used in the invention within particular ranges. Among those preferred are up to 0.013% weight by volume of benzalkonium chloride, up to 0.013% weight by volume of benzethonium chloride, up to 0.5% weight by volume of chlorobutanol, up to 0.004% weight by volume or phenylmercuric acetate or nitrate, up to 0.01% weight by volume of thimerosal, and from about 0.01% to about 0.2% weight by volume of methyl or propylparabens.

Formulations for injection are preferably designed for single-use administration and do not contain preservatives. Injectable solutions should have isotonicity equivalent to 0.9% sodium chloride solution (osmolality of 290-300 mOsmoles). This may be attained by addition of sodium chloride or other co-solvents as listed above, or excipients such as buffering agents and antioxidants, as listed above. Injectable formulations are sterilized and, in one embodiment, supplied in single-use vials or ampules. In another embodiment, injectable products may be supplied as sterile, freeze-dried solids for reconstitution and subsequent injection.

The tissues of the anterior chamber of the eye are bathed by the aqueous humor, while the retina is under continuous exposure to the vitreous. These fluids/gels exist in a highly reducing redox state because they contains antioxidant compounds and enzymes. Therefore, it may be advantageous to include a reducing agent in the ophthalmologic compositions formulated in accordance with the invention, or to dose separately with a reducing agent to maintain the hydroxylamine in its reduced form.

Preferred reducing agents may be N-acetylcysteine, ascorbic acid or a salt form, and sodium sulfite or metabisulfite, with ascorbic acid and/or N-acetylcysteine or glutathione being particularly suitable for injectable solutions. A combination of N-acetylcysteine and sodium ascorbate may be used in various formulations. A metal chelator antioxidant, such as EDTA (ethylenediaminetetraacetic acid) or possibly DTPA (diethylenetriaminepentaacetic acid) may also be added to keep the hydroxylamine in the reduced form in the eye drop formulation.

Compositions utilized in accordance with the methods of the invention may be delivered to the eye of a patient in one or more of several delivery modes known in the art. In a preferred embodiment, the compositions are topically delivered to the eye in eye drops or washes. In another embodiment, the compositions are delivered in a topical ophthalmic ointment, which is particularly useful for treating conditions of the cornea, conjuctiva or surrounding skin, such as dry-eye and blepharitis. In another embodiment, the compositions may be delivered to various locations within the eye via periodic subconjunctival or intraocular injection, or by infusion in an irrigating solution such as BSS® or BSS PLUS® (Alcon USA, Fort Worth, Tex.) or by using preformulated solutions of the viral vectors (or other delivery expression vectors) or CARD protein (e.g. TatCARD) in excipients such as BSS® or BSS PLUS®. In one embodiment, the use of the compounds of the invention in vitrectomy may be effective in reducing or preventing the development of vitrectomy-associated cataracts.

Alternatively, the compositions may be applied in other ophthalmologic dosage forms known to those skilled in the art, such as pre-formed or in situ-formed gels or liposomes, for example as disclosed in U.S. Pat. No. 5,718,922 to Herrero-Vanrell. A direct injection of drugs into the vitreous body used for treating diseases has been used, in which microspheres or liposomes were used to release drugs slowly (Moritera, T. et al. "Microspheres of biodegradable polymers as a drug-delivery system in the vitreous" *Invest. Ophthalmol. Vis. Sci.* 1991 32(6):1785-90).

In another embodiment, the composition may be delivered to or through the lens of an eye in need of treatment via a contact lens (e.g., Lidofilcon B, Bausch & Lomb CW79 or DELTACON (Deltafilcon A) or other object temporarily resident upon the surface of the eye. For example, U.S. Pat. No. 6,410,045 describes a contact lens-type drug delivery device comprising a polymeric hydrogel contact lens containing drug substance in a concentration of between 0.05% and 0.25% by weight absorbed in said contact lens which is capable of being delivered into the ocular fluid.

In other embodiments, supports such as a collagen corneal shield (e.g., B10-COR dissolvable corneal shields, Summit Technology, Watertown, Mass.) can be employed. The compositions can also be administered by infusion into the eyeball, either through a cannula from an osmotic pump (ALZET®, Alza Corp., Palo Alto, Calif.) or by implantation of timed-release capsules (OCCUSENT®) or biodegradable disks (OCULEX®, OCUSERT®) which contain the compositions. These routes of administration have the advantage of providing a continuous supply of the composition to the eye. This may be an advantage for local delivery of the hydroxylamine compounds to the cornea and aqueous humor, for example.

Several other types of ocular devices/delivery systems are available that are particularly suitable for delivering pharmaceutical compositions to the interior or posterior of the eye. For instance, U.S. Pat. No. 6,154,671 to Parel et al. discloses a device for transferring a medicament into the eyeball by iontophoresis. The device utilizes a reservoir for holding the active agent, which contains at least one active surface electrode facing the eye tissue lying at the periphery of the cornea. The reservoir also has a return electrode in contact with the patient's partly closed eyelids. U.S. Pat. No. 5,869,079 to Wong et al. discloses combinations of hydrophilic and hydrophobic entities in a biodegradable sustained release ocular implant. In addition, U.S. Pat. No. 6,375,972 to Guo et al., U.S. Pat. No. 5,902,598 to Chen et al., U.S. Pat. No. 6,331,313 to Wong et al., U.S. Pat. No. 5,707,643 to Ogura et al., U.S. Pat. No. 5,466,233 to Weiner et al. and U.S. Pat. No. 6,251,090 to Avery et al. each describes intraocular implant devices and systems that may be used to deliver pharmaceutical compositions comprising compounds of the present invention.

Other examples of ocular devices pertain to ocular implants for drug delivery are known in the art. Such devices could be loaded with agents of the invention for delivery to the eye. The following is a non-limiting list of representative examples ocular devices for administration to the eye:

U.S. Pat. No. 6,726,918 describes methods for treating inflammation-mediated conditions of the eye comprising: implanting into the vitreous of the eye of an individual a biodegradable implant comprising a steroidal anti-inflammatory agent and a biodegradable polymer, wherein the implant delivers the agent to the vitreous in an amount sufficient to reach a concentration equivalent to at least about 0.05 µg/ml dexamethasone within about 48 hours and maintains a concentration equivalent to at least about 0.03 µg/ml dexamethasone for at least about three weeks.

U.S. Pat. No. 6,713,081 describes ocular implant devices for the delivery of a therapeutic agent to an eye in a controlled and sustained manner. Dual mode and single mode drug delivery devices are illustrated and described. Implants suitable for subconjunctival and intravitreal placement are described. The patent also describes fabrication and implementation techniques associated with the ocular implant devices.

U.S. Pat. No. 6,251,090 describes an intravitreal medicine delivery device, method and implant device through which a wide variety of beneficial medicines including drugs or other pharmacological agents can be introduced into the vitreous cavity over an extended period of time with only a single initial surgery to implant the device. The device and method minimize the surgical incision needed for implantation and avoid future or repeated invasive surgery or procedures. Additional amounts of the initial medicine can readily be introduced or the medication can be varied or changed, as required. Furthermore, the device and method allow the dosage delivered to the vitreous cavity to be controlled and allows the patient to control the timing of the delivery. The device is constructed so as to filter medicines delivered to the cavity and also avoids damage to or interference with other parts of the eye during implantation or during use.

U.S. Pat. No. 5,824,072 describes biocompatible ocular implants comprising active agents that are employed for introduction into a suprachoroidal space or an avascular region of an eye for therapeutic purposes. The administration of drugs is controlled and maintained for long periods of time, while ensuring the substantial absence of significant levels outside the site of administration.

U.S. Pat. No. 5,773,019 describes a continuous release drug delivery implant which, among other mentioned places, can be mounted either on the outer surface of the eye or within the eye. A drug core is covered by a polymer coating layer that is permeable to the low solubility agent without being release rate limiting.

U.S. Pat. No. 5,773,021 describes bioadhesive ophthalmic inserts that are placed in the conjunctival sac. The inserts are prepared by extrusion, thermoforming, or heat compression of a polymeric material matrix and the drug to be delivered. The polymeric matrix comprises a water-soluble biocompatible polymer, such as hydroxyalkyl celluloses, maltodextrins, chitosans, modified starches or polyvinyl alcohols; a water-insoluble biocompatible polymer such as an alkyl cellulose. Where applicable, a bioadhesive polymer such as polyvinyl carboxylic acid type polymers or certain bioadhesive polysaccharides or derivatives thereof may be used. The ophthalmic inserts are characterized therein as intended for the prolonged and controlled release of a medicinal substance.

U.S. Pat. Nos. 5,443,505 and 5,766,242 disclose implants comprising active agents for introduction into a suprachoroidal space or an avascular region of the eye, and describe placing microcapsules and plaques comprising hydrocortisone into the pars plana.

U.S. Pat. No. 5,378,475 describes a sustained-release implant for insertion into the vitreous of the eye. The implant has a first impermeable coating, such as ethylene vinyl acetate, surrounding most, but not all, of a drug reservoir and a second permeable coating, such as a permeable crosslinked polyvinyl alcohol, disposed over the first coating including the region where the first coating does not cover the drug reservoir, to provide a location through which the drug can diffuse out of the implant.

U.S. Pat. No. 5,725,493 describes an ocular implant device for providing drugs to the vitreous cavity over a period of time. The drug reservoir is attached to the outside of the eye with a passageway permitting medicament to enter the vitreous cavity of the eye.

U.S. Pat. No. 5,164,188 discloses encapsulated agents for introduction into the suprachoroid of the eye, and describes placing microcapsules and plaques comprising hydrocortisone into the pars plana.

U.S. Pat. No. 4,997,652 discloses biodegradable ocular implants comprising microencapsulated drugs, and describes implanting microcapsules comprising hydrocortisone succinate into the posterior segment of the eye.

U.S. Pat. No. 4,014,335 describes an ocular drug delivery device placed in the cul-de-sac between the sclera and lower eyelid for administering the drug and acting as a reservoir. The ocular device is characterized therein as administering drug to the eye in a controlled, continuous dosage rate over a prolonged time. To accomplish this, the ocular device comprises a three-layered laminate of polymeric materials holding the drug in a central reservoir region of the laminate. The drug diffuses from the reservoir through at least one of the polymeric layers of the laminate.

U.S. Pat. No. 4,300,557 teaches a capsule which can be filled with a pharmaceutical drug to be delivered which serves as an intraocular implant. The capsule is inserted in the vitreous region of the eye by making an incision in the eye, inserting the capsule and closing the incision. The capsule remains in place for a period of time and may be removed by making a second surgical incision into the eye and retrieving the device. The capsule has an attached tube which passes through the surface of the eye and extends outward from the eye useful for the subsequent injection of a drug. While in the vitreous, the device is not anchored and may move about freely. Further, Zhou et al. discloses a multiple-drug implant comprising 5-fluorouridine, triamcinolone, and human recombinant tissue plasminogen activator for intraocular management of proliferative vitreoretinopathy (PVR) (Zhou, T, et al. 1998, "Development of a multiple-drug delivery implant for intraocular management of proliferative vitreoretinopathy" J. Controlled Release 55:281-295).

According to certain embodiments, compositions including agents are formulated and administered so as to apply a dosage effective for alleviating oxidative stress in the interior and posterior of the eye, and/or inhibiting the development of macular degeneration, other retinopathies or uveitis in the eye, among other utilities as discussed herein. In general, it may be preferred that the active amount be from about 0.1% to about 10.0% weight by volume in the formulation. In some embodiments, it is preferable that the active drug concentration be 0.25% to about 10.0% weight by volume. The concentration of the hydroxylamine component will preferably be in the range of about 0.1 μM to about 10 mM in the tissues and fluids. In some embodiments, the range is from 1 μm to 5 mM, in other embodiments the range is about 10 μM to 2.5 mM. In other embodiments, the range is about 50 μM to 1 mM. Most preferably the range of hydroxylamine concentration will be from 1 to 100 μM. The concentration of the reducing agent will be from 1 μM to 5 mM in the tissues and fluids, preferably in the range of 10 μM to 2 mM. The concentrations of the components of the composition are adjusted appropriately to the route of administration, by typical pharmacokinetic and dilution calculations, to achieve such local concentrations.

Other forms of administration, wherein the delivery to the eye is not called for, may include oral tablets, liquids and sprays; intravenous, intramuscular, intraarterial, subcutaneous and intraperitoneal injections; application to the skin as a patch or ointment; enemas, suppositories, or aerosols.

The compositions of the invention may contain at least one adjunct compound in addition to an agent of the invention, wherein the adjunct compound is useful for treating a disease or disorder that is the target of the agent of the invention. Thus the compositions may include a therapeutic agent and an adjunct compound. The agent and compound(s) may be administered sequentially or concurrently. Similarly, the methods of the invention include using such combination therapy.

For effective treatment of macular degeneration or any of the other retinopathies or eye conditions described herein, one skilled in the art may recommend a dosage schedule and dosage amount adequate for the subject being treated. It may be preferred that dosing occur one to four times daily for as long as needed. The dosing may occur less frequently if the compositions are formulated in sustained delivery vehicles, or are delivered via implant or intravitreal injection. The dosage schedule may also vary depending on the active drug concentration, which may depend on the hydroxylamine used and on the needs of the patient.

An ophthalmologist or one similarly skilled in the art will have a variety of means to monitor the effectiveness of the dosage scheme and adjust dosages accordingly. For example, effectiveness in the treatment of macular degeneration or other retinopathies may be determined by improvement of visual acuity and evaluation for abnormalities and grading of stereoscopic color findus photographs. (Age-Related Eye Disease Study Research Group, NEI, NIH, AREDS Report No. 8, 2001, Arch. Ophthalmol. 119: 1417-1436). Effectiveness in the treatment of uveitis may be determined by improvement in visual acuity and vitreous haze and control of inflammation (Foster et al., 2003, Arch. Ophthalmol. 121: 437-40). Following such evaluation, the ophthalmologist may adjust the frequency and/or concentration of the dose, if needed.

Ilustrative Examples

Methods:

Methods Summary: The CARD (caspase activation and recruitment domain) was amplified from the human apoptosis-associated speck-like protein containing a CARD (ASC) gene and fused to the cell-penetrating peptide sequence derived from the HIV Tat protein using PCR. The product was fused to either a puromycin resistance gene in a lentiviral vector plasmid or to a secretable form of GFP through a furin cleavage site. The sequence of the TatCARD insert was verified by DNA sequencing and cloned in an AAV plasmid. The monocytic cell line THP-1 and the retina pigmented ephitelium like cell line ARPE-19 were transduced with lentiviral vectors to generate stable cell lines by selecting for puromycin resistant cells. Expression of Tat-CARD was determined by western blot, and its biological effect on LPS or 4-HNE induced secretion of IL-1β was measured by ELISA. Cellular localization of the secretable TatCARD was determined by fluorescent microscopy. Detection of secreted TatCARD was inferred western blot using cell conditioned media.

Cell Culture. The HEK293T cell line was grown in DMEM media supplemented with 10% fetal bovine serum (FBS) and 1% penicillin-streptomycin (Pen-Strep) solution. The ARPE-19 cell line was obtained from ATCC, which validated its identity. Cell stocks were frozen upon arrival and passaged fewer than 4 times before being discarded. ARPE19 cells were grown in DMEM/F12 (50/50) media supplemented with 10% FBS and 1% Pen-Strep. THP-1 cells were grown in RPMI-1640 supplemented with 10% FBS and 1% Pen-Strep. All the cell cultures were maintained in an incubator at 37° C. with 5% $CO_2$. All stable cell lines generated by lentiviral vector transduction were grown in the corresponding media supplemented with puromycin at a dose of 1 µg/mL.

Transfection. Cells were plated at 8×10⁵ cells per well in a 6-well plate with complete growth medium and incubated for 24 hours. The next day, complete growth medium was replaced in each well with 2 mL of serum- and antibiotic-free medium. Plasmid DNA complexes were generated by diluting 4 µg of the corresponding DNA in 100 µL of sterile phosphate buffered saline (PBS) and 10 µg of a 1 µg/µL of polyethyleneimine[28] (PEI) in 100 µL of PBS. Dilutions were incubated at room temperature for 5 minutes. DNA:PEI complexes were made by mixing the diluted DNA and PEI and incubating them for 20 minutes at room temperature. Complexes were overlaid on the cells drop wise and cells were maintained at 37° C. for 18 hours. The transfection was stopped by removing the complex-containing medium and replacing it with 3 mL of complete growth medium. Cells were grown for another 24 hours at 37° C. Afterwards, cells were harvested by trypsin treatment and centrifugation.

Viral Vectors. All the lentiviral vectors were created using the pCDH-EF1-MCS-T2A-Puro plasmid (Systems Biosciences, Mountain View Calif.). The transgenes were cloned using the EcoRI and the NotI restriction sites in the multiple cloning sites. Plasmids were grown in DH5α cells and sequenced by the Sanger method[29]. To generate viral particles, the plasmids were co-transfected with the pPACKH1 lentivector packaging kit (Systems Biosciences, Mountain View Calif.) in HEK293T cells. The lentiviral vector containing media were harvested at 48 hours after the co-transfection and were centrifuged at 3,000 rpm for 5 minutes at 4° C. These vector containing media were filtered using a 0.22 µm syringe filter.

Immunoprecipitation. ARPE-19 cells expressing either TatCARD or only the puromycin resistance gene were disrupted in NP-40 lysis buffer (1% NP-40, 150 mM NaCl, 50 mM Tris-Cl pH 8.0) supplemented with Protease Inhibitors Cocktail (Thermo Fisher Scientific, Rockford Ill.) and 2 mM EDTA. Samples were kept on ice for 20 minutes and mixed by vortexing every ten minutes followed by a centrifugation at 16,000×g for 15 minutes at 4° C. Lysate was collected, and the protein concentration of the was measured with the DC Protein Assay (Bio-Rad, Hercules Calif.) according to the manufacturer's protocol. Lysates were diluted to 1 µg/µl. A total of 500 µg of lysate was incubated with 1 µg of normal rabbit IgG antibody (Santa Cruz Biotechnology, Dallas Tex.) and 20 µL protein A/G-agarose beads (Santa Cruz Biotechnology, Dallas Tex.) at 4° C. for 1 hour in a rotating mixer. Beads were pelleted by centrifugation at 1,000×g for 5 minutes at 4° C. A total of 5 µg of anti-Caspase-1 antibody (Millipore) were added to 20 µg protein A/G-agarose beads in a total volume of 500 µL PBS and were incubated at 4° C. for 1 hour in a rotating mixer. Antibody/beads complex was pelleted by centrifugation as done previously and was resuspended in 500 µL of 0.2M triethanolamine pH 8.3 containing 20 mM of the cross-linking agent dimethyl pimelimidate (Sigma-Aldrich, St Louis Mo.). The complexes were incubated for 1 hour at room temperature in a rotating mixer. The cross-linking reaction was quenched by adding 50 µL of 1M Tris-HCl pH 7.5 and incubating for 1 hour at room temperature in a rotating mixer. The complexes were pelleted by centrifuging as done previously. The complexes were washed with 500 µL of 0.2 M glycine HCl pH 2.5 by incubating them for 1 minute at room temperature in a rotating mixer. These complexes were then washed 3 times with PBS containing 0.01% Tween-20. A total of 500 µL of diluted lysate (500 µg protein) was used to resuspend the pellet. Samples were kept at 4° C. overnight in a rotating mixer. The next day, samples were centrifuged at 1,000×g for 5 minutes at 4° C. Supernatant was removed and the pellet was washed 4 times with NP-40 lysis buffer by resuspending and centrifuging as in previous steps. After the last wash, the pellet was resuspended in 60 µL of Laemmlli sample buffer and boiled for 5 minutes. Samples were centrifuged at 16,000×g for 10 seconds, and supernatant was transferred to a new 1.5 mL microcentrifuge tube. A total of 20 µL of sample were analyzed in a 12% SDS polyacrylamide gel and transferred onto PVDF membranes using the iBlot system. Membranes were probed with anti-Caspase-1 (Millipore, 1:1000 dilution) or anti-T2A (Millipore, 1:1000 dilution)

Enzyme Linked Immunosorbent Assay (ELISA). Medium was harvested from the indicated cultures and 100 µL aliquots were used to quantify IL-1β concentration. The ELISA kit for the human IL-1β was purchased from RayBiotech (Norcross, Ga.). The concentration of IL-1β was determined according to the manufacturer's protocol.

Western Blot. Cells were disrupted as described above. Protein lysates were diluted in Laemmli sample buffer containing 100 µM DTT and boiled for 5 minutes. Equal amounts of protein were separated by SDS polyacrylamide gel electrophoresis and transferred into a PVDF membrane using the iBlot system (Invitrogen, Grand Island, N.Y.). This membrane was blocked with a proprietary blocking buffer from Li-Cor (Li-Cor Biosciences, Lincoln, Ne.) for 1 hour at room temperature and incubated overnight with the designated primary antibody at 4° C.

Endotoxin-Induced Uveitis (EIU) mouse model. Mice of the C57B/6 strain were injected in the vitreous of each eye with $3 \times 10^9$ vector genomes of AAV2 expressing either GFP or sGFP-TatCARD from the CMV enhancer-chicken beta actin (CBA) promoter. One month after the injection GFP expression was observed by fluorescent funduscopy. The next day, mice were injected intravitreally in each eye with 25 ng of LPS. After 24 hours, these mice were sacrificed by inhalation with $CO_2$ followed by thoracotomy, and their eyes were enucleated and placed in 4% paraformaldehyde at 4° C. overnight. Eyes were embedded in paraffin were sectioned through the cornea-optic nerve axis at a thickness of 12 μm. The sections were collected in independent slides with sections on the same slide having a difference of 96 μm. Slides were stained with hematoxylin and eosin to visualize infiltrating cells. These cells were counted in images of the sections by two independent observers.

Fundoscopy. We used digital fundus imaging with a Micron III retinal imaging microscope (Phoenix Research Laboratories, Pleasaton, Calif.) to monitor gene expression. Conscious mice had their eyes dilated with 1% atropine and 10% phenylephrine. Mice were then anesthetized with a mixture of ketamine and xylazine in normal saline. To avoid loss of moisture from the ocular surface during the procedure mice received a drop of 2.5% hypermellose ophthalmic demulcent solution (Gonak, AKORN, Lake Forest, Ill.). B. Using the fluorescein filters we measure GFP fluorescence using the same exposure time for all the eyes.

Statistical Analysis. Statistical analysis was performed using the Graphpad Prism 5 software. Averages of replicate experiments were compared by ANOVA followed by the Newman-Keuls test to detect differences among all groups. Statistical significance was reported whenever the calculated p-value was ≤0.05.

Results: The expression of the TatCARD significantly inhibited the LPS induced secretion of IL-1β from THP-1 cells. The cellular distribution of sGFP-TatCARD in transfected cells was punctate in contrast to the cytoplasmic distribution of GFP. The fused sGFP-TatCARD construct was detected in tranfected cell lysates, whereas the cleaved GFP was detected in the corresponding cell conditioned media. Stable ARPE-19 cells transduced with either empty lentivector control or TatCARD lentivector were stimulated with 4-HNE at 300 for 24 hours. The levels of secreted IL-1β in the conditioned media were lower in cells expressing the TatCARD construct than in the empty lentivector control cells.

Conclusions: The expression of TatCARD inhibits the LPS and the 4-HNE induced secretion of IL-1β. We have successfully constructed a secretable form of the TatCARD protein that may be useful in blocking retinal and RPE inflammation.

Although more than one route can be used to administer a particular agent, a particular route can provide a more immediate and more effective reaction than another route. Accordingly, the described routes of administration are merely exemplary and are in no way limiting.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

What is claimed is:

1. A method for the amelioration or treatment of an ocular disease or ocular condition in a subject, the method comprising:
    intravitreally administering a therapeutically effective amount of a viral vector comprising an expression construct comprising (a) a nucleotide sequence encoding a fusion protein comprising a cell-penetrating peptide derived from the HIV Tat protein (Tat) and a Caspase Activation and Recruitment Domain (CARD) and (b) a nucleotide sequence encoding a secretion signal peptide to the subject's eye, wherein the Tat comprises amino acids 1-9 of the amino acid sequence of SEQ ID NO: 1 and the CARD comprises amino acids 10-100 of the amino acid sequence of SEQ ID NO: 1
    wherein the ocular disease or ocular condition is selected from the group consisting of ocular inflammation, macular degeneration, age-related macular degeneration (AMD), geographic atrophy, wet AMD, dry AMD, drusen formation, dry eye, diabetic retinopathy, vitreoretinopathy, corneal inflammation, uveitis, ocular hypertension and glaucoma.

2. The method of claim 1, wherein said viral vector is an AAV vector.

3. The method of claim 1, wherein said viral vector is a retroviral vector, a lentiviral vector, an adenoviral vector, a Herpes viral vector, a Hepatitis viral vector, an SV40 vector, an EBV vector, an adeno-associated virus (AAV) vector or a nonviral vector.

4. The method of claim 1, wherein said method comprises treating a subject who exhibits one or more of the following symptoms: drusen formation, eye pain, eye redness, light sensitivity, tearing, or blurred vision.

5. The method of claim 4, wherein said method comprises treating a subject who exhibits two or more of the following symptoms: drusen, eye pain, eye redness, light sensitivity, tearing, or blurred vision.

6. The method of claim 4, wherein said subject exhibits drusen formation.

7. The method of claim 2, wherein the AAV vector is an AAV2 vector.

8. The method of claim 1, wherein the secretion signal peptide is an IgK signal peptide.

* * * * *

UNITED STATES PATENT AND TRADEMARK OFFICE
CERTIFICATE OF CORRECTION

PATENT NO. : 10,981,961 B2
APPLICATION NO. : 14/775289
DATED : April 20, 2021
INVENTOR(S) : Cristhian J. Ildefonso et al.

Page 1 of 1

It is certified that error appears in the above-identified patent and that said Letters Patent is hereby corrected as shown below:

On the Title Page

Please add the following item (60):
Related U.S. Application Data
(60) Provisional application No. 61/776,076 filed on Mar. 11, 2013.

Signed and Sealed this
Twenty-fourth Day of September, 2024

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 100
<212> TYPE: PRT
<213> ORGANISM: Artificial Sequence

```
<220> FEATURE:
<223> OTHER INFORMATION: Synthetic Polypeptide

<400> SEQUENCE: 1

Arg Lys Lys Arg Arg Gln Arg Arg Gln Ser Ala Ala Lys Pro Gly
1               5                   10                  15

Leu His Phe Ile Asp Gln His Arg Ala Ala Leu Ile Ala Arg Val Thr
                20                  25                  30

Asn Val Glu Trp Leu Leu Asp Ala Leu Tyr Gly Lys Val Leu Thr Asp
            35                  40                  45

Glu Gln Tyr Gln Ala Val Arg Ala Glu Pro Thr Asn Pro Ser Lys Met
        50                  55                  60

Arg Lys Leu Phe Ser Phe Thr Pro Ala Trp Asn Trp Thr Cys Lys Asp
65                  70                  75                  80

Leu Leu Leu Gln Ala Leu Arg Glu Ser Gln Ser Tyr Leu Val Glu Asp
                85                  90                  95

Leu Glu Arg Ser
            100

<210> SEQ ID NO 2
<211> LENGTH: 303
<212> TYPE: DNA
<213> ORGANISM: Artificial Sequence
<220> FEATURE:
<223> OTHER INFORMATION: Sythetic Polynucleotide

<400> SEQUENCE: 2
cgcaagaagc gccgccagcg ccgccgccag tcggcagcca agccaggcct gcactttata      60
gaccagcacc gggctgcgct tatcgcgagg gtcacaaacg ttgagtggct gctggatgct     120
ctgtacggga aggtcctgac ggatgagcag taccaggcag tgcgggccga gcccaccaac     180
ccaagcaaga tgcggaagct cttcagtttc acaccagcct ggaactggac ctgcaaggac     240
ttgctcctcc aggccctaag ggagtcccag tcctacctgg tggaggacct ggagcggagc     300
tga                                                                    303
```